United States Patent
Bronkalla et al.

(10) Patent No.: US 11,024,029 B2
(45) Date of Patent: Jun. 1, 2021

(54) VASCULAR DISSECTION DETECTION AND VISUALIZATION USING A SUPERIMPOSED IMAGE WITH AN IMPROVED ILLUSTRATION OF AN OUTERMOST VESSEL PERIPHERY

(71) Applicant: INTERNATIONAL BUSINESS MACHINES CORPORATION, Armonk, NY (US)

(72) Inventors: Mark D. Bronkalla, Waukesha, WI (US); Ben Graf, Charlestown, MA (US); Arkadiusz Sitek, Ashland, MA (US); Yiting Xie, Cambridge, MA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/507,840

(22) Filed: Jul. 10, 2019

(65) Prior Publication Data
US 2021/0012496 A1    Jan. 14, 2021

(51) Int. Cl.
*G06T 7/00* (2017.01)
*G06T 7/66* (2017.01)
(Continued)

(52) U.S. Cl.
CPC .............. *G06T 7/0014* (2013.01); *G06T 7/12* (2017.01); *G06T 7/66* (2017.01); *G08B 21/02* (2013.01);
(Continued)

(58) Field of Classification Search
CPC ........... G06T 7/0014; G06T 7/12; G06T 7/66; G06T 2207/20081; G06T 2207/30172;
(Continued)

(56) References Cited

U.S. PATENT DOCUMENTS

2008/0033302 A1   2/2008   Grady et al.
2010/0166283 A1*  7/2010   Grosskopf .............. G06T 7/149
                                               382/131
(Continued)

OTHER PUBLICATIONS

Dehghan et al. "Automatic Detection of Aortic Dissection in Contrast-Enhanced CT." 14th International Symposium on Biomedical Imaging, Apr. 18, 2017, pp. 557-560 (Year: 2017).*

(Continued)

*Primary Examiner* — Jon Chang
(74) *Attorney, Agent, or Firm* — Michael Best & Friedrich LLP

(57) ABSTRACT

Methods and systems for detecting a dissection of an elongated structure in a three dimensional medical image. One system includes an electronic processor that receives the three dimensional medical image. The electronic processor determines a first periphery and a second periphery of the elongated structure, the first periphery and the second periphery associated with an enhancing part and a non-enhancing part, respectively, of the elongated structure. The electronic processor determines whether the first periphery or the second periphery best illustrates an outermost periphery of the elongated structure and generate a base image based on whether the first periphery or the second periphery best illustrates an outermost periphery of the elongated structure. The electronic processor superimposes a contrast image associated with the three dimensional image on top of the base image, detects a dissection in the elongated structure using the superimposed image, and outputs a medical report identifying the dissection.

20 Claims, 20 Drawing Sheets
(13 of 20 Drawing Sheet(s) Filed in Color)

(51) Int. Cl.
*G06T 7/12* (2017.01)
*G16H 30/40* (2018.01)
*G08B 21/02* (2006.01)

(52) U.S. Cl.
CPC ... *G16H 30/40* (2018.01); *G06T 2207/20081* (2013.01); *G06T 2207/30101* (2013.01); *G06T 2207/30172* (2013.01)

(58) Field of Classification Search
CPC .......... G06T 2207/30101; G08B 21/02; G16H 30/40
See application file for complete search history.

(56) References Cited

U.S. PATENT DOCUMENTS

| | | |
|---|---|---|
| 2011/0206257 A1 | 8/2011 | Qanadli et al. |
| 2018/0068437 A1 | 3/2018 | Bronkalla et al. |
| 2019/0021677 A1 | 1/2019 | Grbic et al. |
| 2019/0105008 A1* | 4/2019 | Dehghan Marvast ...................... A61B 6/5217 |

OTHER PUBLICATIONS

Duan et al. "Automatic Aortic Dissection Recognition Based on CT Images." Proceedings of the 2nd International Conference on Biomedical Engineering and Bioinformatics, Sep. 2018, pp. 55-59 (Year: 2018).*

Xiaojie et al. "Segmentation of the Aortic Dissection from CT Images Based on Spatial Continuity Prior Model." 8th International Conference on Information Technology in Medicine and Education, Dec. 23, 2016, pp. 275-280 (Year: 2016).*

J. Li, "Multi-Task Deep Convolutional Neural Network for the Segmentation of Type B Aortic Dissection." (Submitted on Jun. 26, 2018 (v1), last rev. Nov. 22, 2018 (this version, v6)) https://arxiv.org/abs/1806.09860.

H. Hong and U. Sheikh, "Automatic detection, segmentation and classification of abdominal aortic aneurysm using deep learning," 2016 IEEE 12th International Colloquium on Signal Processing & Its Applications (CSPA), Malacca City, 2016, pp. 242-246.

J. Oria, "Computational Intelligence for Abdominal Aortic Aneurysm Imaging Analysis," Ph.D. Dissertation, Department of Electronic Technology, The University of the Basque Country, Donostia—San Sebastián, 2013.

K. López-Linares, "Fully automatic detection and segmentation of abdominal aortic thrombus in post-operative CTA images using deep convolutional neural networks." (Submitted on Apr. 1, 2018) https://arxiv.org/abs/1804.00304.

D. Vukadinovic, "Segmentation of the Outer Vessel Wall of the Common Carotid Artery in CTA," in IEEE Transactions on Medical Imaging, vol. 29, No. 1, pp. 65-76, Jan. 2010.

J. Shum, "Quantitative Assessment of Abdominal Aortic Aneurysm Geometry." Annals of Biomedical Engineering 39 (1): 277-86, Oct. 2010.

United States Patent Office Action for U.S. Appl. No. 16/507,842 dated Oct. 2, 2020 (10 pages).

U.S. Appl. No. 16/507,840, filed Jul. 10, 2019.
U.S. Appl. No. 16/507,829, filed Jul. 10, 2019.
U.S. Appl. No. 16/507,842, filed Jul. 10, 2019.

United States Patent Office Action for U.S. Appl. No. 16/507,829 dated Jan. 26, 2021 (11 pages).

Lohou et al., "Augmented Digitally Reconstructed Radiographs of Aortic Dissection CTA Images," 5th International Conference on BioMedical Engineering and Informatics, Oct. 16, 2012, pp. 103-107.

Xu et al., "An Automated Detection Scheme of Acute Stanford Type A Aortic Dissection Based on DCNNs in CTA Images," Proceedings of the 4th International Conference on Multimedia Systems and Signal Processing, May 10, 2019, pp. 16-20.

United States Patent Office Notice of Allowance for U.S. Appl. No. 16/507,842 dated Jan. 25, 2021 (9 pages).

United States Patent Office Examiner Initiated Interview Summary for U.S. Appl. No. 16/507,842 dated Jan. 14, 2021 (1 page).

* cited by examiner

VASCULAR DISSECTION DETECTION AND VISUALIZATION USING A SUPERIMPOSED IMAGE WITH AN IMPROVED ILLUSTRATION OF AN OUTERMOST VESSEL PERIPHERY

FIELD

Embodiments described herein relate to vascular dissection detection and visualization, notably those consistent with Acute Aortic Syndrome ("AAS").

SUMMARY

Three dimensional medical scanners, such as X-ray computed tomography (CT) scanners and magnetic resonance imaging (MRI) scanners, are used to capture three dimensional images of the interior of the human body. The amount of information generated by three dimensional medical scanners is staggering, and the large amount of information generated by the three dimensional medical scanners puts a large cognitive load and time constraint on a radiologist reviewing the information for abnormalities. Advances in computerized image analysis and deep learning (artificial intelligence software or systems) are easing the cognitive load put on radiologists by providing ways to review three dimensional medical images for abnormalities faster and semi-automatically (or fully automatically).

However, to determine the centerline of the elongated structure using artificial intelligence software, such as a convolutional neural network, the artificial intelligence software must be trained. Training the artificial intelligence software requires a training set of three dimensional images with marked or known centerlines. Also, a different training set needs to be developed for each elongated structure being processed by artificial intelligence software. Developing a training set is a time consuming and laborious process. For example, to create a training example included in the training set a user must manually determine the centerline of the elongated structure in the applicable image by marking the location of the centerline on each slice of a three dimensional image that includes the centerline. For example, FIGS. 1A and 1B illustrate two slices of a three dimensional medical image. The slice illustrated in FIG. 1A is an axial view, and the slice illustrated in FIG. 1B is a coronal view. In existing systems, a user may need to accurately mark a centerline in each of the slices to include these slices in the training information for the artificial intelligence software. Accordingly, building a set of training information in this manner is a laborious process.

To speed up the process of creating a training set for training artificial intelligence software, embodiments described herein provide systems and methods for building a training set for an artificial intelligence system, which is used to train the artificial intelligence system to automatically determine the centerline of an elongated structure. The training set may include one or more training examples and each training example may be generated based on a plurality of reference points marked (manually) in a subset of slices of three dimensional medical images, such as one or more reference points provided in every predetermined number of slices. After the centerline of an elongated structure is determined, the centerline is used to detect abnormalities in the elongated structure. Thus, embodiments described herein provide systems and methods for determining an abnormality in an elongated structure in a three dimensional medical image.

For example, one embodiment provides a system for determining an abnormality in an elongated structure in a three dimensional medical image. The system includes an electronic processor. The electronic processor is configured to determine a centerline of the elongated structure in the three dimensional medical image and determine a plurality of two dimensional cross sections of the three dimensional medical image based on the centerline. For each two dimensional cross section of the plurality of two dimensional cross sections, the electronic processor is configured to convert the two dimensional cross section to polar coordinates, fit a line to the elongated structure in the two dimensional cross section converted to polar coordinates, and reconvert the two dimensional cross section to Cartesian coordinates.

Another embodiment provides a method of determining an abnormality in an elongated structure in a three dimensional medical image. The method includes determining a centerline of the elongated structure in the three dimensional medical image and determining a plurality of two dimensional cross sections of the three dimensional medical image based on the centerline. The method also includes, for each two dimensional cross section of the plurality of two dimensional cross sections, converting the two dimensional cross section to polar coordinates, fitting a line to the elongated structure in the two dimensional cross section converted to polar coordinates, and reconverting the two dimensional cross section to Cartesian coordinates.

Yet another embodiment provides a system for generating a training example to train artificial intelligence software to automatically determine a centerline of an elongated structure of three dimensional images. The system includes an electronic processor that is configured to receive a plurality of reference points for a subset of a plurality of slices of a first three dimensional image and receive a selection of a starting reference point within the plurality of reference points. Each of the plurality of reference points marks a centerline of the elongated structure within one of the subset of the plurality of slices. The electronic processor is also configured to determine an order of the plurality of reference points and fit a spline curve to the plurality of reference points based on the order of the reference points to define a marked centerline of the three dimensional image to create the training example. The electronic processor is further configured to add the training example to a training set and use the training set to train the artificial intelligence software to automatically determine a centerline of an elongated structure in a second three dimensional medical image.

A further embodiment provides a method of generating a training example to train artificial intelligence software to automatically determine a centerline of an elongated structure of three dimensional images. The method includes receiving a plurality of a reference points for a subset of a plurality of slices of a first three dimensional image and receiving a selection of a starting reference point within a plurality of reference points. Each of the plurality of reference points marking a centerline of the elongated structure within one of the subset of the plurality of slices. The method also includes determining an order of the plurality of reference points and fitting a spline curve to the plurality of reference points based on the order reference points based on the order of the reference points to define a marked centerline of the three dimensional image to create a training example. The method further includes adding the training example to a training set and using the training set to train the artificial intelligence software to automatically determine a centerline of an elongated structure in a second three dimensional image.

Additionally, Acute Aortic Syndrom ("AAS") abnormalities, most notably aortic dissections are a significant cause of death and complications. In particular, dissections of the aorta, which are associated with dissections, occur when layers of the vessel wall separate and tear and, in many cases, the separation rapidly progresses, which can lead to a rupture and death. Mortality rates for acute undiagnosed aortic dissections are in the range of 1-2% per hour. Detection of other AAS features, such as hematoma and ulcerations may also be desirable. Additionally, classification of a dissection type (for example, Stanford A or B), a dissection location, and an extent of a lesion may also be desirable Visualization of a dissection is very difficult via standard means, which often include contrast enhanced CT and ultrasound. The dissected flap is quite thin as the intima is approximately 100 micrometer and the media layer is less than 1 millimeter. Both the intima and media layer are also radiolucent, which makes them hard to render on CT scans due to their small size (for example, being on the order of the pixel size) and due to the fact that they are low in contrast versus vascular plaques or calcifications that are commonly visualized in existing products. For example, in a typical abdominal CT with resolution of 512×512, the pixel dimension are on the order of 0.9 millimeter to 1.0 millimeter. Due to this, partial volume effects further reduce the visibility of the dissection. An abdominal aorta ultrasound does not have sufficient resolution, and conventional x-ray angiography or digital subtraction angiography will typically obscure the dissection. Cineangiography may show a dissection in some cases, as a swirling flow pattern if viewed from the proper angle, but this is not the standard procedure for imaging some anatomy.

To address these and other issues, embodiments described herein provide enhanced visualization of a dissection, which may be poorly visible or partially obscured on a contrast exam and almost invisible in a non-contrast exam. Alternatively or in addition, embodiments described herein provide enhanced visualization of atheromatous plaque (for example, large atheromatous plaque that is vulnerable for rupture), thrombus, and intramural haematoma. Embodiments described herein provide enhanced conspicuity of the dissection and also provide prioritization of the studies containing the detected dissection so that the studies may be quickly read by a radiologist (worklist prioritization). The embodiments are described herein in the context of chest and abdomen CT studies. However, the embodiments described herein may be implemented in the context of other studies and are not limited to chest and abdomen CT studies. Other examples of studies to which the embodiments described herein may be applicable include peripheral vascular studies (for example, iliac or femoral arteries) or neurovascular studies (for example, carotid or vertebral arteries).

For example, one embodiment provides a system for detecting a dissection in an elongated structure in a three dimensional medical image. The system includes an electronic processor configured to receive the three dimensional medical image and determine a periphery of the elongated structure included in the three dimensional medical image. The electronic processor is also configured to generate a non-contrast image representing the periphery of the elongated structure and superimpose a contrast image associated with the three dimensional image on top of the non-contrast image to generate a superimposed image. The electronic processor is also configured to detect at least one dissection in the elongated structure using the superimposed image and output a medical report identifying the at least one dissection detected in the elongated structure.

Another embodiment provides a method for detecting a vascular dissection in an elongated structure in a three dimensional medical image. The method includes receiving, with an electronic processor, the three dimensional medical image. The method also includes determining, with the electronic processor, a periphery of the elongated structure included in the three dimensional medical image. The method also includes generating, with the electronic processor, a non-contrast image representing the periphery of the elongated structure. The method also includes superimposing, with the electronic processor, a contrast image associated with the three dimensional image on top of the non-contrast image to generate a superimposed image. The method also includes detecting, with the electronic processor, at least one dissection of the elongated structure using the superimposed image. The method also includes outputting, with the electronic processor, a medical report identifying the at least one dissection detected in the elongated structure.

Yet another embodiment provides a non-transitory computer readable medium including instructions that, when executed by an electronic processor, causes the electronic processor to execute a set of functions. The set of functions includes receiving the three dimensional medical image and determining a periphery of the elongated structure included in the three dimensional medical image. The set of functions also includes generating a non-contrast image representing the periphery of the elongated structure and superimposing a contrast image associated with the three dimensional image on top of the non-contrast image to generate a superimposed image. The set of functions also includes detecting at least one dissection of the elongated structure using the superimposed image and outputting a medical report identifying the at least one dissection detected in the elongated structure.

Yet another embodiment provides a system for detecting a vascular dissection in an elongated structure in a three dimensional medical image. The system includes an electronic processor configured to receive the three dimensional medical image and determine a first periphery of the elongated structure included in the three dimensional medical image. The first periphery is associated with an enhancing part of the elongated structure. The electronic processor is also configured to determine a second periphery of the elongated structure included in the three dimensional medical image. The second periphery is associated with a non-enhancing part of the elongated structure. The electronic processor is also configured to determine whether the first periphery or the second periphery best illustrates an outermost periphery of the elongated structure and generate a base image representing either the first periphery of the elongated structure or the second periphery of the elongated structure based on whether the first periphery or the second periphery best illustrates an outermost periphery of the elongated structure. The electronic processor is also configured to superimpose a contrast image associated with the three dimensional image on top of the base image to generate a superimposed image. The electronic processor is also configured to detect at least one dissection in the elongated structure using the superimposed image and output a medical report identifying the at least one dissection detected in the elongated structure.

Yet another embodiment provides a method for detecting a vascular dissection in an elongated structure in a three dimensional medical image. The method includes receiving, with an electronic processor, the three dimensional medical image. The method also includes determining, with the electronic processor, a first periphery of the elongated structure included in the three dimensional medical image. The first periphery is associated with an enhancing part of the elongated structure. The method also includes determining, with the electronic processor, a second periphery of the elongated structure included in the three dimensional medical image. The second periphery is associated with a non-enhancing part of the elongated structure. The method also includes determining, with the electronic processor, whether the first periphery or the second periphery best illustrates an outermost periphery of the elongated structure. The method also includes generating, with the electronic processor, a base image representing either the first periphery of the elongated structure or the second periphery of the elongated structure based on whether the first periphery or the second periphery best illustrates an outermost periphery of the elongated structure. The method also includes superimposing, with the electronic processor, a contrast image associated with the three dimensional image on top of the base image to generate a superimposed image. The method also includes detecting, with the electronic processor, at least one dissection in the elongated structure using the superimposed image. The method also includes outputting, with the electronic processor, a medical report identifying the at least one dissection detected in the elongated structure.

Yet another embodiment provides a non-transitory computer readable medium including instructions that, when executed by an electronic processor, causes the electronic processor to execute a set of functions. The set of functions includes receiving the three dimensional medical image and determining a first periphery of the elongated structure included in the three dimensional medical image. The first periphery is associated with an enhancing part of the elongated structure. The set of functions also includes determining a second periphery of the elongated structure included in the three dimensional medical image. The second periphery is associated with a non-enhancing part of the elongated structure. The set of functions also includes determining whether the first periphery or the second periphery best illustrates an outermost periphery of the elongated structure and generating a base image representing either the first periphery of the elongated structure or the second periphery of the elongated structure based on whether the first periphery or the second periphery best illustrates an outermost periphery of the elongated structure. The set of functions also includes superimposing a contrast image associated with the three dimensional image on top of the base image to generate a superimposed image and detecting at least one dissection in the elongated structure using the superimposed image. The set of functions also includes outputting a medical report identifying the at least one dissection detected in the elongated structure.

Yet another embodiment provides a system for detecting a vascular dissection in an elongated structure in a three dimensional medical image. The system includes an electronic processor configured to receive the three dimensional medical image and detect a centerline of the elongated structure in the three dimensional medical image. The electronic processor is also configured to determine a plurality of two dimensional cross sections of the three dimensional medical image based on the centerline. For each of the plurality of two dimensional cross sections, the electronic processor is configured to determine a radial density profile and determine a density gradient based on the radial density profile for each of the plurality of two dimensional cross sections. The electronic processor is also configured to analyze one or more of a plurality of density gradients determined for each of the plurality of two dimensional cross sections. The electronic processor is also configured to detect at least one dissection in the elongated structure included in the three dimensional medical image based on the analysis of the density gradient for each of the plurality of two dimensional cross sections and output a medical report identifying the at least one dissection detected in the elongated structure.

Yet another embodiment provides a method for detecting a vascular dissection in an elongated structure in a three dimensional medical image. The method includes receiving, with an electronic processor, the three dimensional medical image. The method also includes detecting, with the electronic processor, a centerline of the elongated structure in the three dimensional medical image, and determining, with the electronic processor, a plurality of two dimensional cross sections of the three dimensional medical image based on the centerline. The method also includes, for each of the plurality of two dimensional cross sections, determining, with the electronic processor, a radial density profile and determining, with the electronic processor, a density gradient based on the radial density profile for each of the plurality of two dimensional cross sections. The method also includes analyzing, with the electronic processor, one or more of a plurality of density gradients determined for each of the plurality of two dimensional cross sections. The method also includes detecting, with the electronic processor, at least one dissection in the elongated structure included in the three dimensional medical image based on the analysis of the density gradient for each of the plurality of two dimensional cross sections and outputting, with the electronic processor, a medical report identifying the at least one dissection detected in the elongated structure.

Yet another embodiment provides a non-transitory computer readable medium including instructions that, when executed by an electronic processor, causes the electronic processor to execute a set of functions. The set of functions includes receiving the three dimensional medical image and detecting a centerline of the elongated structure in the three dimensional medical image. The set of functions also includes determining a plurality of two dimensional cross sections of the three dimensional medical image based on the centerline. The set of functions also includes, for each of the plurality of two dimensional cross sections, determining a radial density profile and determining a density gradient based on the radial density profile for each of the plurality of two dimensional cross sections. The set of functions also includes analyzing one or more of a plurality of density gradients determined for each of the plurality of two dimensional cross sections. The set of functions also includes detecting at least one dissection in the elongated structure included in the three dimensional medical image based on the analysis of the density gradient for each of the plurality of two dimensional cross sections, and outputting a medical report identifying the at least one dissection detected in the elongated structure.

Other aspects of the embodiments will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1B:
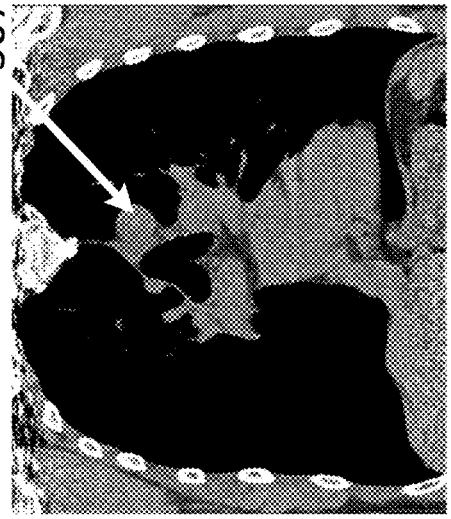
FIG. 1B illustrates an example of a coronal slice of a three dimensional medical image of a torso including a reference point.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As noted above, embodiments described herein provide systems and methods for generating a training set including a plurality of training examples for training artificial intelligence software to detect a centerline in a three dimensional image, such as a medical image. As described in more detail below, to create a training example for the training set, a user places a reference point within a predetermined number or frequency of slices in a three dimensional medical image marking the centerline. The systems and methods described herein use the reference points to determine the centerline of the elongated structure in the three dimensional image, and the three dimensional image with the determined centerline (represented as a plurality of slices) is added to the training set as a training example.

Figure 2:
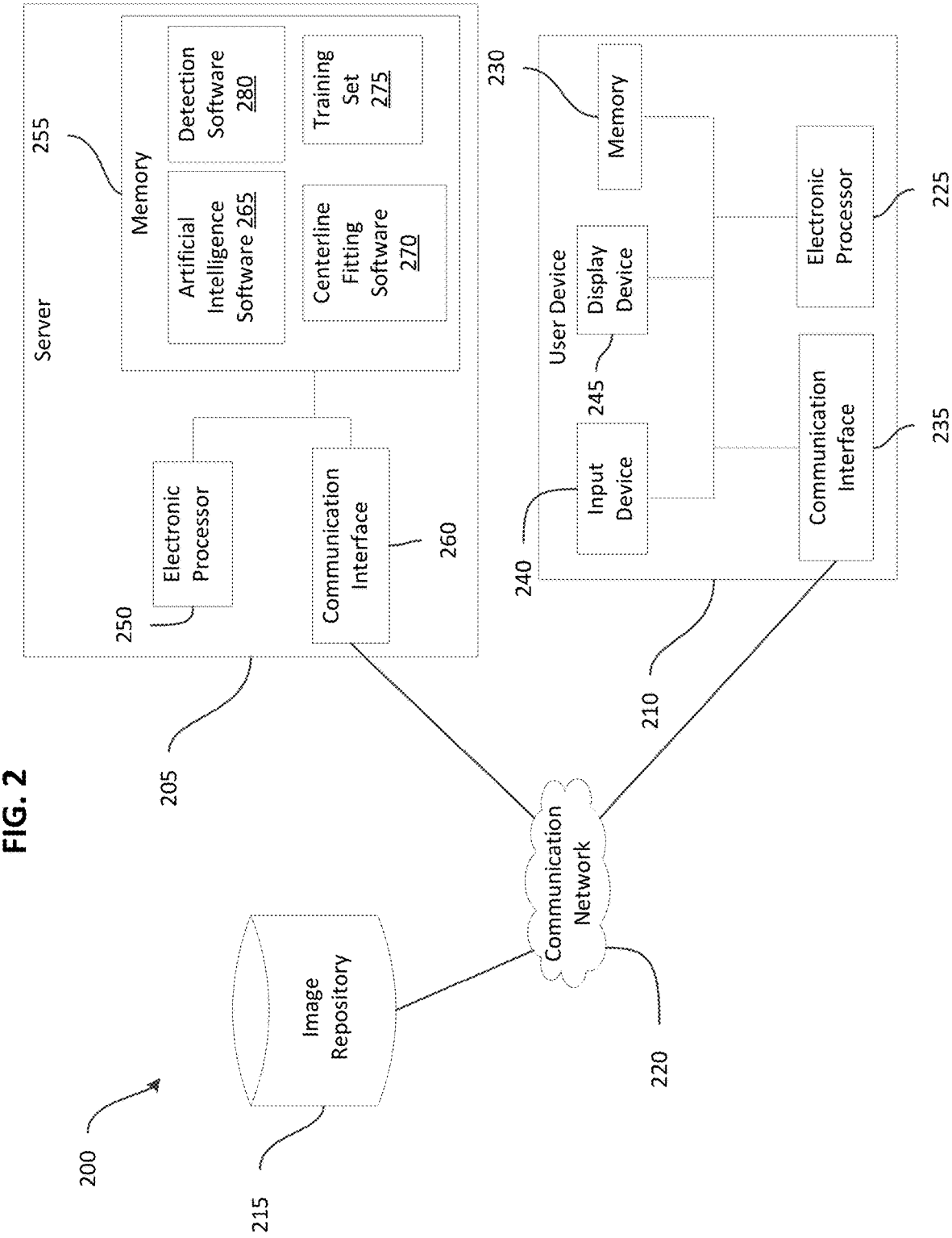
FIG. 2 illustrates a system for generating a training example to train artificial intelligence software to determine a centerline of an elongated structure in a three dimensional image according to one embodiment.

For example, FIG. 2 illustrates a system 200 for generating a centerline of an elongated structure in a three dimensional image according to one embodiment. As illustrated in FIG. 2, the system 200 includes a server 205, a user device 210, and an image repository 215. The user device 210, server 205, and image repository 215 communicate over one or more wired or wireless communication networks 220. Portions of the wireless communication networks 220 may be implemented using a wide area network, such as the Internet, a local area network, such as a Bluetooth™ network or Wi-Fi, and combinations or derivatives thereof. It should be understood that each server included in the system 200 may communicate with a different number of user devices, and the user devices 210 illustrated in FIG. 2 are purely for illustrative purposes. Similarly, it should also be understood that the system 200 may include more or fewer servers and the single server 205 illustrated in FIG. 2 is purely for illustrative purposes. It should also be understood that the system 200 may include more or fewer image repositories and the single image repository 215 is purely for illustrative purposes. Also, in some embodiments, the user device 210 may communicate with the server 205 through one or more intermediary devices (not shown).

The user device 210 includes an electronic processor 225, a memory 230, a communication interface 235, an input device 240, and a display device 245. The electronic processor 225, memory 230, communication interface 235, input device 240, and display device 245 communicate wirelessly, over wired communication channels or buses, or a combination thereof. The user device 210 may include additional components than those illustrated in FIG. 2 in various configurations. For example, in some embodiments, the user device 210 includes multiple electronic processors, multiple memory modules, multiple input devices, multiple display devices, multiple communication interfaces, or a combination thereof. For example, although only a single input device 240 is illustrated in FIG. 2, in some embodiments, the user device 210 may include multiple input devices, for example, a keypad, a keyboard, a mouse, a touchscreen (for example, as part of the display device 245), a microphone, a camera, or the like (not shown). Also, it should be understood that the functionality described herein as being performed by the user device 210 may be performed in a distributed nature by a plurality of computers located in various geographic locations. For example, the functionality described herein as being performed by the user device 210 may be performed by a plurality of computers included in a cloud computing environment. Similarly, in some embodiments, the functionality described herein as being performed by the user device 210, or a portion thereof, may be performed by the server 205.

The electronic processor 225 included in the user device 210 may be a microprocessor, an application-specific integrated circuit (ASIC), and the like. The electronic processor 225 is generally configured to execute software instructions to perform a set of functions, including the functions described herein or a portion thereof. The memory 230 includes a non-transitory computer-readable medium and stores data, including instructions that are executable by the electronic processor 225. The communication interface 235 may be, for example, a wired or wireless transceiver or port, for communicating over the communication network 220 and, optionally, one or more additional communication networks or connections.

The display device 245 may be, for example, a touch-screen, a liquid crystal display (LCD), a light-emitting diode (LED) display, an organic LED (OLED) display, an electroluminescent display (ELD), or the like for displaying information to a user of the user device 210. Similarly, the input device 240 includes a device for receiving information from a user, such as, for example, a keypad, a keyboard, a mouse, a touchscreen (for example, as part of the display device 245), a microphone, a camera, or the like.

In some embodiments, three dimensional images including elongated structures are stored in the image repository 215. The image repository 215 may be, for example, a picture archiving and communication system (PACS), a cloud storage environment, or the like. The three dimensional images stored in the image repository 215 are generated by an imaging modality (not shown), such as an X-ray computed tomography (CT) scanner, a magnetic resonance imaging (Mill) scanner, or the like. In some embodiments, the image repository 215 may also be included as part of an imaging modality.

The user device 210 communicates with image repository 215 via the communication interface 235 to request and receive a three dimensional image from the image repository 215. A user may request specific images from the image repository for review or the user device 210 may be configured to automatically request images, such as by requesting available images meeting various parameters (for example, imaging modality, anatomical structure, patient demographic, or the like). The user device 210 displays received three dimensional images on the display device 245 (as a three dimensional image or as a plurality of two-dimensional slices forming the three-dimensional image (see example slices illustrated in FIGS. 1A and 1B)). The user device 210 also receives a plurality of reference points for a displayed three-dimensional image from a user via the input device 240. As described in more detail below, the plurality of reference points may include one or more reference points in each of a subset of the slices of the three-dimensional image, such as one or more reference points in every predetermined (Nth) slice of the image. The received reference points mark points on a center line of an elongated structure in the three dimensional image. The reference points may not be received in any particular order, however, in some embodiments, a selection of a starting reference point is received via the input device 240. The user device 210 may send the three dimensional image and the associated reference points to the server 205 via the communication interface 235.

As illustrated in FIG. 2, the server 205 includes an electronic processor 250, a memory 255, and a communication interface 260. The electronic processor 225, memory 230, and communication interface 235 communicate wirelessly, over wired communication channels or buses, or a combination thereof. The server 205 may include additional components than those illustrated in FIG. 2 in various configurations. For example, in some embodiments, the server 205 includes multiple electronic processors, multiple memory modules, multiple communication interfaces, or a combination thereof. Also, it should be understood that the functionality described herein as being performed by the server 205 may be performed in a distributed nature by a plurality of computers located in various geographic locations. For example, the functionality described herein as being performed by the server 205 may be performed by a plurality of computers included in a cloud computing environment.

The electronic processor 250 may be a microprocessor, an application-specific integrated circuit (ASIC), and the like. The electronic processor 250 is generally configured to execute software instructions to perform a set of functions, including the functions described herein. The memory 255 includes a non-transitory computer-readable medium and stores data, including instructions that are executable by the electronic processor 250. The communication interface 260 may be, for example, a wired or wireless transceiver or port, for communicating over the communication network 220 and, optionally, one or more additional communication networks or connections. As illustrated in FIG. 2, the memory 255 of the server 205 includes artificial intelligence software 265, centerline fitting software 270, and a training set 275. It should be understood that, in some embodiments, the functionality described herein as being provided by the artificial intelligence software 265 and centerline fitting software 270 may be distributed and combined in various configurations. The artificial intelligence software 265 may be, for example, supervised machine learning software such as a neural network, a Bayesian network, a support vector machine, or the like. In some embodiments, the memory 255 also includes detection software 280. The detection software 280 is, for example, medical diagnostic software. The type of medical diagnostic software the detection software 280 is may be dependent on the elongated structure the artificial intelligence software 265 is trained to detect the centerline of. For example, in some embodiments, the artificial intelligence software 265 is trained to detect the centerline of an aorta (or other major artery), a colon, an esophagus, or a different elongated anatomical structure.

The artificial intelligence software 265 stored in the memory 255 of the server 205 is configured to automatically determine the centerlines of elongated structures in three dimensional images when executed by the electronic processor 250. The training set 275 includes a plurality of three dimensional images including elongated structures with a marked or known centerline. The training set 275 is provided to the artificial intelligence software 265 to train the software 265 to automatically determine the centerline of an elongated structure in other three dimensional medical images, such as images that have not yet been analyzed and, thus, do not have marked or known centerlines. Training the artificial intelligence software 265 includes presenting the artificial intelligence software 265 with a plurality of images that have elongated structures with unmarked but known centerlines (the training set 275). For each of the three dimensional images, the artificial intelligence software 265 predicts the location of the centerline of the elongated structure in the three dimensional image. The prediction of the location of the centerline made by the artificial intelligence software 265 is compared to the known location of the centerline in the three dimensional image. In response to a difference (exceeding a minimum threshold) between the location of the centerline determined by the artificial intelligence software 265 and the known location of the centerline in the three dimensional image, adjustments are made to the artificial intelligence software 265. The process of predicting the location of the centerline, comparing the predicted location of the centerline with the known correct centerline location, and adjusting the artificial intelligence software 265 is repeated until the artificial intelligence software 265 predicts the location of the centerline with at least a predetermined level of accuracy.

Figure 1A:
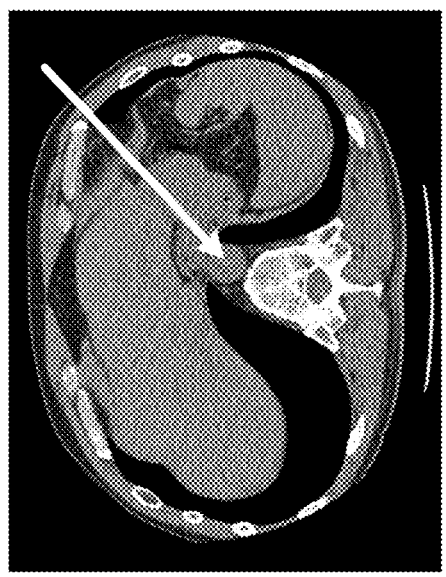
FIG. 1A illustrates an example of an axial slice of a three dimensional medical image of a torso including a reference point.

The centerline fitting software 270 is configured to create the training set 275 for training artificial intelligence software 265. The centerline fitting software 270 is configured to receive, from the user device 210, a three dimensional image and a plurality of reference points associated with the three dimensional image. The reference points are located on the centerline of the elongated structure in the three dimensional image and may be placed within a predetermined number or frequency, such as every predetermined number of slices in the three dimensional image. In some embodiments, the slice that the reference point is placed in may be an axial view slice, as illustrated in FIG. 1A, or a coronal view slice, as illustrated in FIG. 1B, depending on the orientation of the elongated structure in the three dimensional medical image. The centerline fitting software 270 is configured to connect the reference points to automatically determine the centerline of the elongated structure within the three dimensional image, as described below with reference to FIG. 3.

Figure 3:
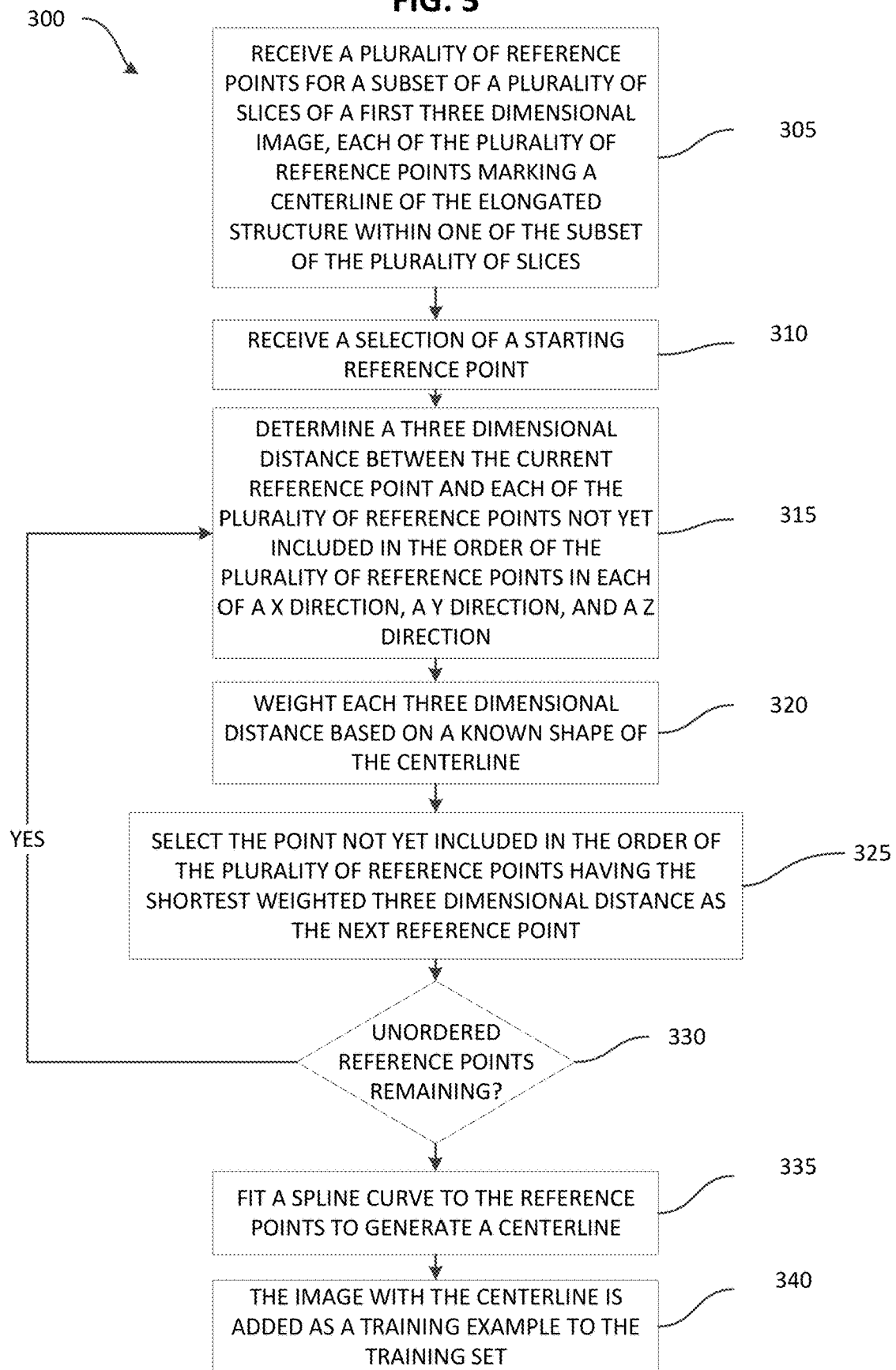
FIG. 3 is a flow chart illustrating a method for generating a training example to train artificial intelligence software to determine a centerline of an elongated structure in a three dimensional image according to one embodiment.

FIG. 3 illustrates a method 300 of generating a training example to train the artificial intelligence software 265 to determine a centerline of an elongated structure in a three dimensional image. The method 300 as described herein may be performed by the system 200 when the centerline fitting software 270 is executed by the electronic processor 250 of the server 205. However, as noted above, the functionality performed by the server 205 may be combined and distributed in various configurations. As illustrated in FIG. 3, the method 300 includes receiving, from the user device 210, a plurality of reference points for a subset of a plurality of slices of a three-dimensional image (at block 305). For example, as noted above, a user may use the input device 240 of the user device 210 to manually add the reference points to the three-dimensional image. In some embodiments, the user device 210 also submits the three-dimensional image associated with the reference points to the server 205. However, in other embodiments, the user device 210 may provide an identifier of the three-dimensional image, which the server 205 may use to access the image from the image repository 215 or another source (for example, a local cache).

As described above, the reference points represent the location of the centerline of the elongated structure in the three dimensional image as manually marked by the user of the user device 210. Each of the plurality of reference points may be included in one of the plurality of slices of the three-dimensional image, and the slices including the reference points may represent a subset of the slices included in the three-dimensional image. For example, in some embodiments, a user provides at least one reference point in at least every predetermined (Nth) number of image slices, such as one or more reference points every ten slices. FIGS. 1A and 1B illustrate example reference points 307A and 307B (pointed to by the white arrows included in these figures for illustration purposes) marked by a user in a slice of a three-dimensional image.

Figure 4:
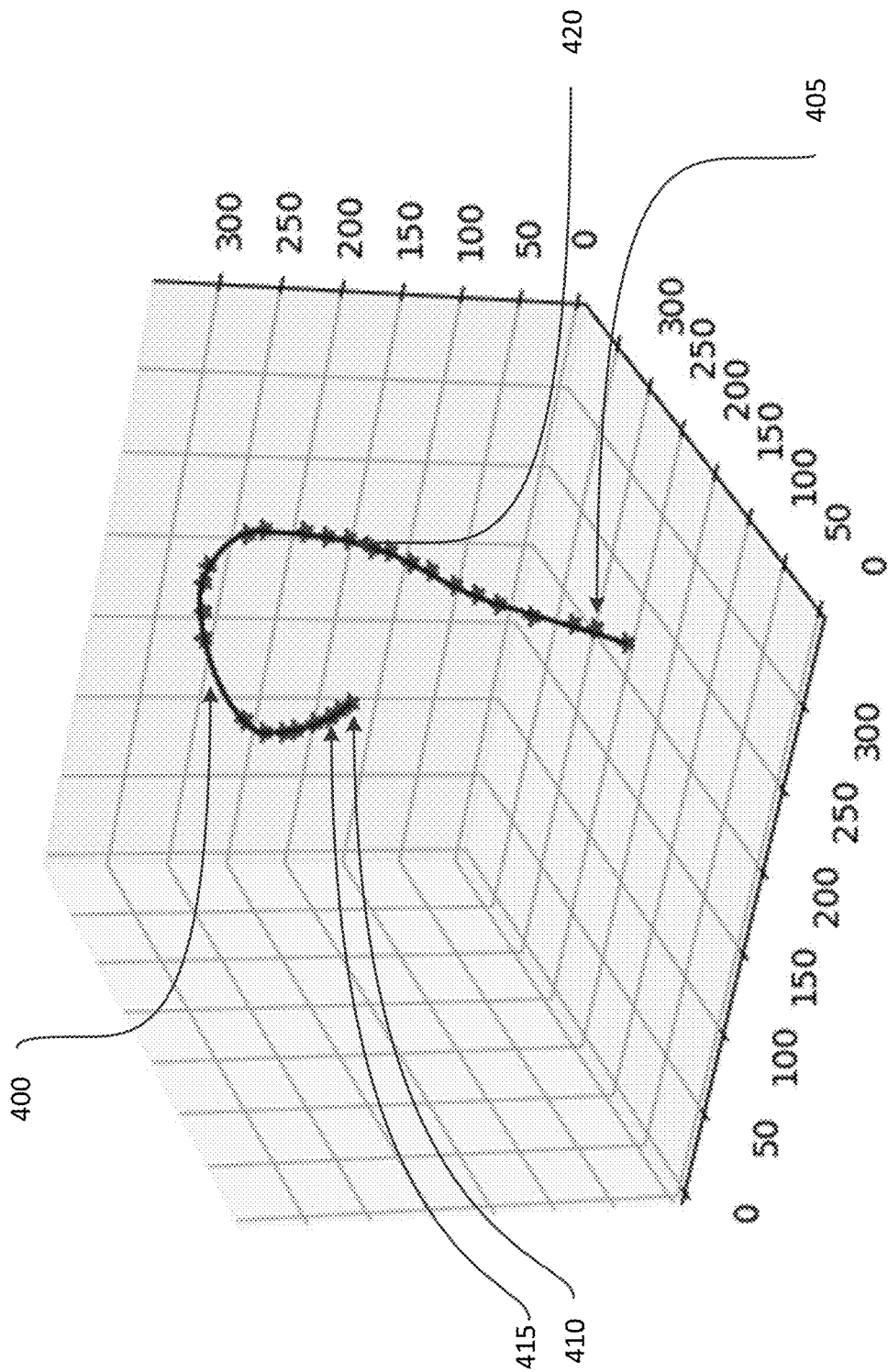
FIG. 4 illustrates an example of a centerline of an elongated structure in three dimensional space that has been determined from a plurality of reference points manually annotated in a subset of slices of a three dimensional image.

In some embodiments, the electronic processor 250 also receives a selection of a starting reference point (at block 310). A user may manually select a starting reference point of the plurality of reference points or the centerline fitting software 270 may be configured to automatically select the starting reference point (for example, based on the order of the reference points, locations of the reference points within the sequences of slices, locations of the reference points within associated slices, or the like). For example, a user may not necessarily provide the reference points in an order corresponding to a dimension of the elongated structure. Accordingly, although the user provides the reference points for the elongated structure, the centerline fitting software 270 may be configured to automatically determine an order of the reference points based on a known shape of the elongated structure. FIG. 4 illustrates an example of a centerline 400 of an elongated structure in three dimensional space determined from a plurality of reference points 405 provided by the user. The units of the axes in FIG. 4 are pixels. In determining the centerline 400, the centerline fitting software 270 may be configured to determine a sequence of points using this known hook shape. For example, when determining the point that follows a point at the end of the hook (for example, the point 410, which may represent a starting reference point), the electronic processor 250 determines the next ordered point along the centerline is the point 415 rather than the point 420 even when the point 420 is closer to the point 410 than the point 415 is in at least one dimension. In particular, the electronic processor 250 sets the point 415 to be the next point rather than the point 420 because the electronic processor 250 weights the distances between reference points in an image based on the position of the reference points in the elongated structure and the expected or known shape as described in further detail below.

For example, beginning with the starting reference point as a current reference point, the electronic processor 250 determines the next reference point in the centerline to determine the order of the reference points, which defines the centerline. The order of the reference points in the centerline is the order that the reference points are connected to represent the centerline. As generally described above, the electronic processor 250 may determine the next reference point by determining a three dimensional distance from the current reference point to each remaining reference point in the three dimensional image that has not been included in the order of the reference points (at block 315). The electronic processor 250 weights each of the determined three dimensional distances with a weight (associates each of the three dimensional determined distances with a weight) that depends on the position of the reference point in a known shape of the elongated structure (for example, if the elongated structure is an artery, an esophagus, or a colon) and an expected position of the next reference point along the known shape of the centerline (block 320). For example, if the centerline for a particular elongated structure has a hook shape and a current point is located at the curved end of the hook, a reference point other than the reference point that is the closest to the current point may be set as the next point. In other words, the electronic processor 250 determines the next reference point to be the reference point with the shortest weighted three dimensional distance from the current reference point that is not yet included in the order of the reference points (at block 325). The electronic processor 250 determines whether there are any reference points in the three dimensional image that are not included in the order of the reference points of the centerline (block 330). While there are reference points in the three dimensional image that have not been included in the order of the reference points in the centerline, the electronic processor 250 proceeds to determine the next reference point in the centerline (block 315). In response to every reference point in the three dimensional image being included in the order of the reference points of the centerline, the electronic processor 250 fits a curve (for example, a spline curve) to the reference points based on the order of the reference points, creating a three dimensional image with a marked centerline (block 335), which is added as a training example to the training set 275 (block 340).

After a plurality of training examples have been determined for an elongated structure and included in the training set 275, the electronic processor 250 uses the training set 275 to train the artificial intelligence software 265 to automatically determine the centerline of an elongated structure in a three dimensional image, such as a three dimensional image that has not been analyzed (with an unknown or unverified centerline).

Figure 5:
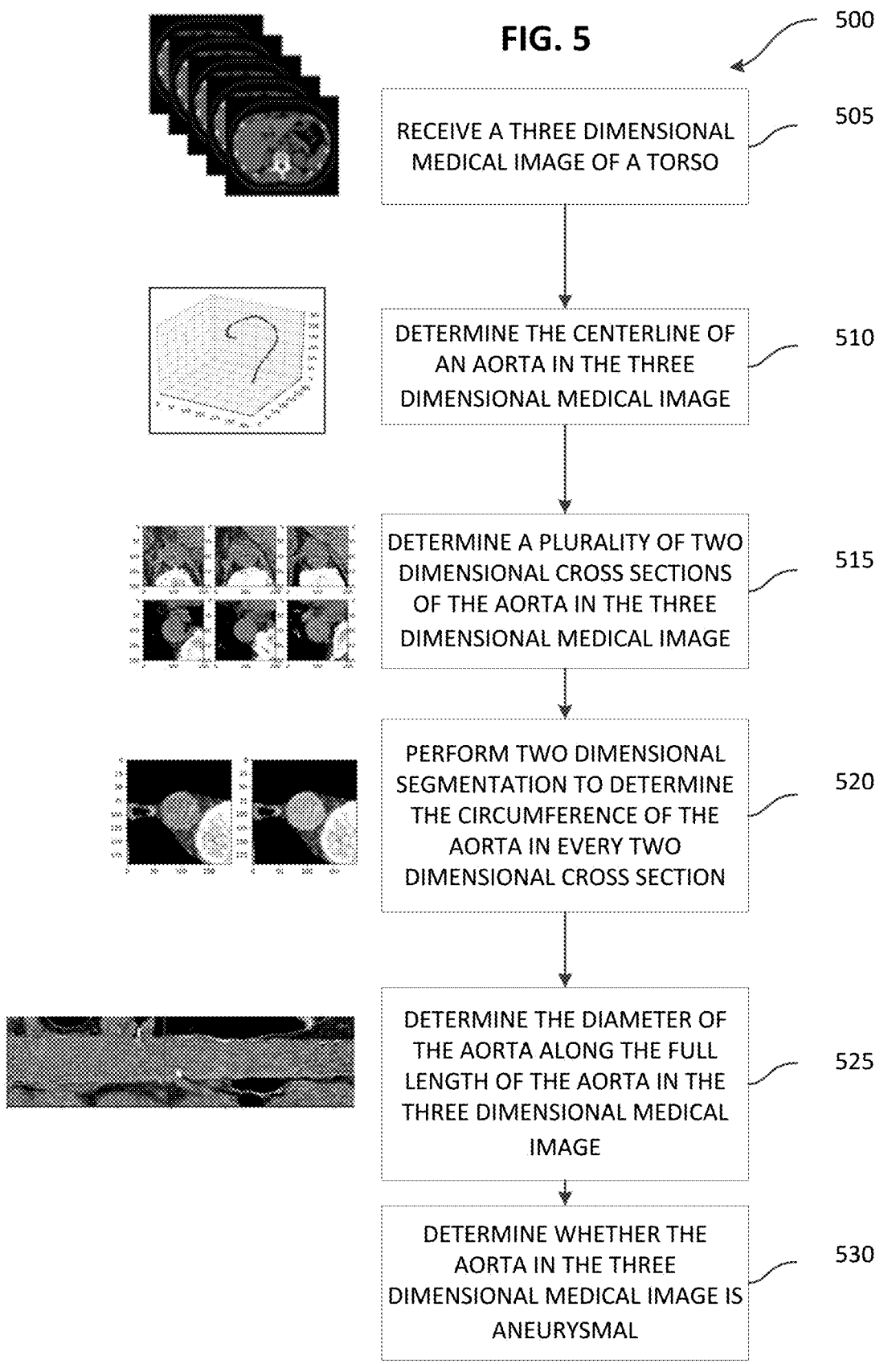
FIG. 5 is a pictorial illustration and a flow chart illustrating a method of determining whether an elongated structure in a three dimensional medical image is aneurysmal according to one embodiment.

After the artificial intelligence software 265 is trained, the artificial intelligence software 265 may be used in combination with the detection software 280 to determine an abnormality in an elongated structure in a three dimensional medical image. For example, FIG. 5 illustrates a method 500, as performed by the system 200 when the electronic processor 250 executes the detection software 280, of determining when an elongated structure in a three dimensional medical image is aneurysmal. As illustrated in FIG. 5, the method 500 includes receiving, with the electronic processor 250, a three dimensional medial image of a torso, such as from the image repository 215 via the communication interface 260 (at block 505). The electronic processor 250 executes the artificial intelligence software 265 to automatically determine the centerline of the aorta in the three dimensional medical image. The artificial intelligence software 265 in this example has been trained using a training set (for example, the training set 275) that includes a plurality of training examples wherein the centerline of the aorta has been determined using the method 300 described above. After the centerline of the aorta is determined in the three dimensional medical image by the artificial intelligence software 265 (at block 510), the electronic processor 250 executes the detection software 280 to determine a plurality of two dimensional cross sections of the aorta in the three dimensional image (at block 515). The electronic processor 250 then performs two dimensional segmentation to determine the circumference of the aorta in every two dimensional cross section (at block 520).

Figure 6:
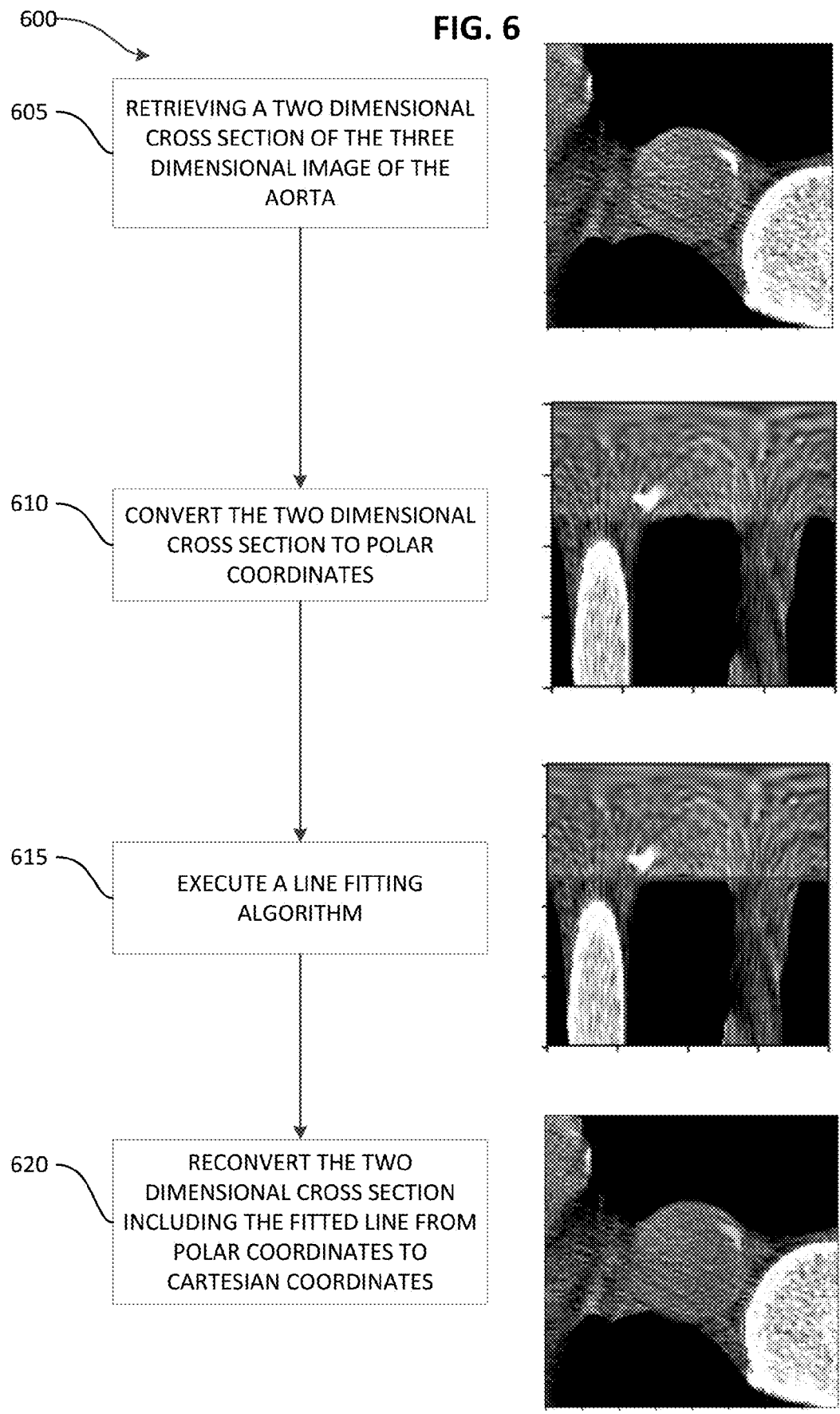
FIG. 6 is a pictorial illustration and a flow chart illustrating a method of determining a two dimensional segmentation on a two dimensional cross section of a three dimensional image of an elongated structure according to one embodiment.

FIG. 6 graphically illustrates a method 600 for performing two dimensional segmentation. The method 600 includes retrieving a two dimensional cross section of the three dimensional medical image of the aorta (at block 605). As shown in FIG. 6, the electronic processor 250 converts the two dimensional cross section to polar coordinates (at block 610). Converting the two dimensional cross section to polar coordinates causes the circumference of the aorta to appear as a semi-straight line. A line fitting algorithm is executed by the electronic processor 250 to fit a line to the perimeter of the aorta (at block 615). The electronic processor 250 reconverts the two dimensional cross section including the fitted line to Cartesian coordinates (at block 620). The area inside the fitted line included in the two dimensional cross section reconverted to Cartesian coordinates is the area of the two dimensional image that includes the aorta. Returning to the method 500, by performing two dimensional segmentation on each two dimensional cross section of the aorta the diameter of the aorta along the full length of the aorta may be determined (at block 525). Using the determined diameters of the aorta, the electronic processor 250 may determine when the aorta in the three dimensional medical image is aneurysmal, such as by determining if the diameter of the aorta ever exceeds a predetermined threshold (block 530).

The methods and systems described herein are also useful in other contexts to detect various medical conditions. For example, as noted above, dissections associated with aortic aneurysms are difficult to detect. Accordingly, embodiments described herein may alternatively or in addition provide enhanced visualization and detection of a vascular dissection, hematoma, or ulcer.

A dissection (a vascular dissection) occurs when a tear of the intima (an inner lining) of a vessel allows blood to leak into the media (the middle layer) of a vessel. Generally, when a dissection occurs, two passageways for blood are created: (1) a normal passageway (a true lumen) and (2) a newly created passageway (a false lumen). With respect to non-contrast images of the vessel, the intima and the media of the vessel are typically too thin and low in contrast to visualize the dissection at an aneurysm.

Figure 7:
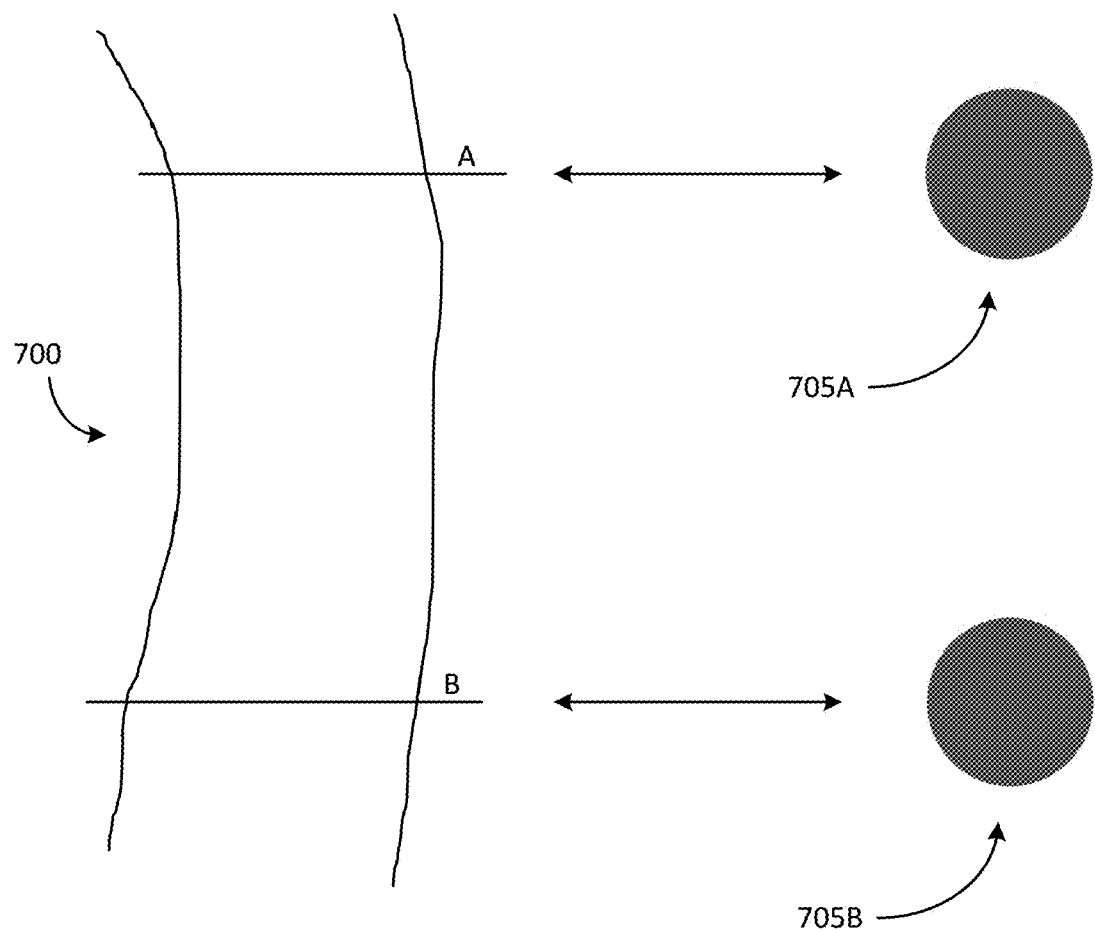
FIG. 7 illustrates a vessel and two cross sections of the vessel.

For example, FIG. 7 illustrates a vessel 700. The vessel 700 illustrated in FIG. 7 is an example of a normal vessel (a true lumen). As illustrated in FIG. 7, two cross sections of the vessel 700 are also illustrated. In particular, a first cross section 705A corresponds with a first cross sectional location A traversing the vessel 700, and a second cross section 705B corresponds with a second cross sectional location B traversing the vessel 700.

Figure 8:
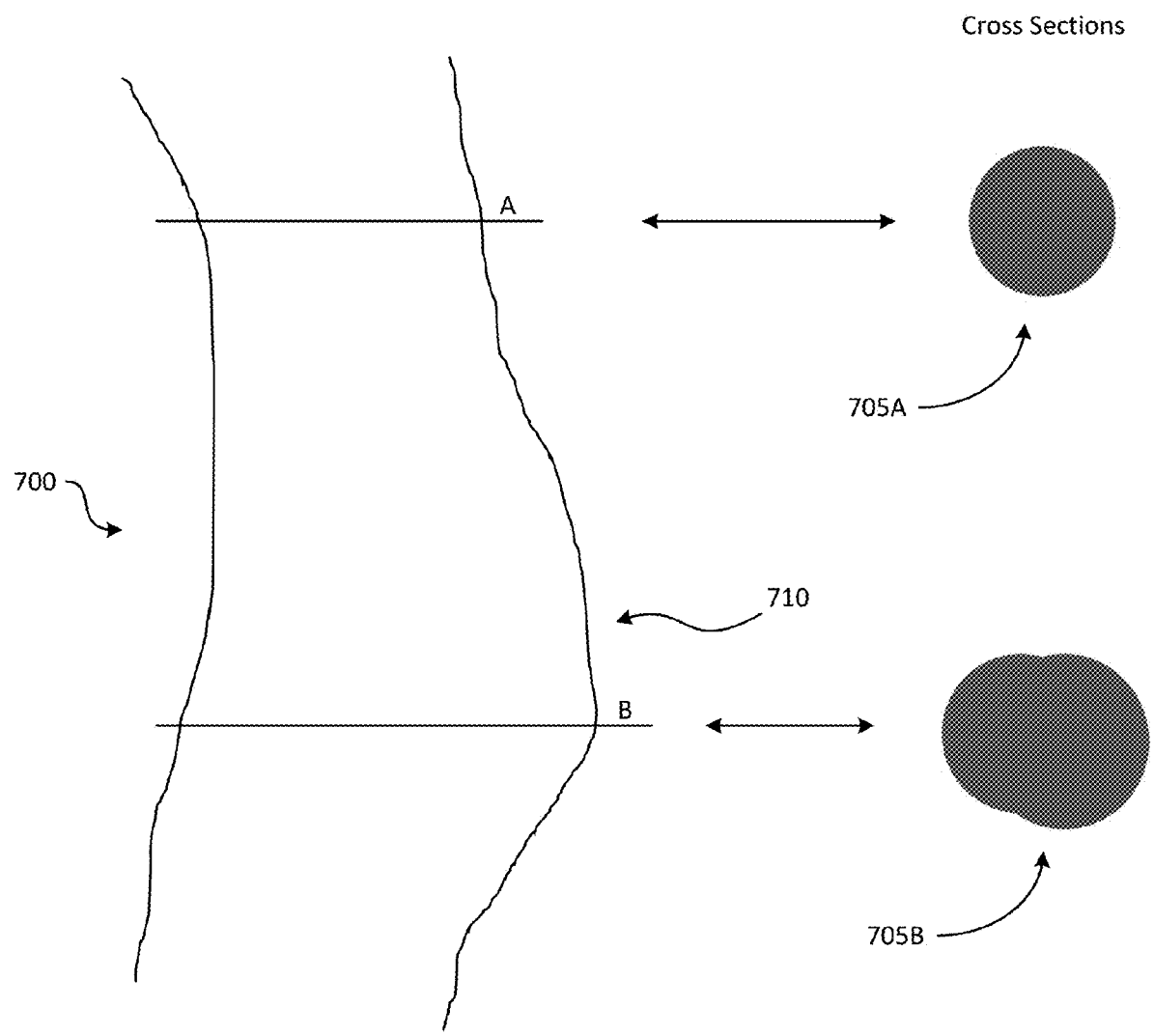
FIG. 8 illustrates the vessel of FIG. 7 with an aneurysm and two cross sections of the vessel with the aneurysm.

FIG. 8 illustrates the vessel 700 with an aneurysm 710 (without contrast). It should be understood that the vessel 700 with the aneurysm 710 is an illustrative example and that, in some cases, a dissection may occur without an aneurysm. As illustrated in FIG. 8, the second cross section 705B takes into account the aneurysm 710 of the vessel 700, which generally causes the vessel 700 to bulge outward in at least one direction.

Figure 9:
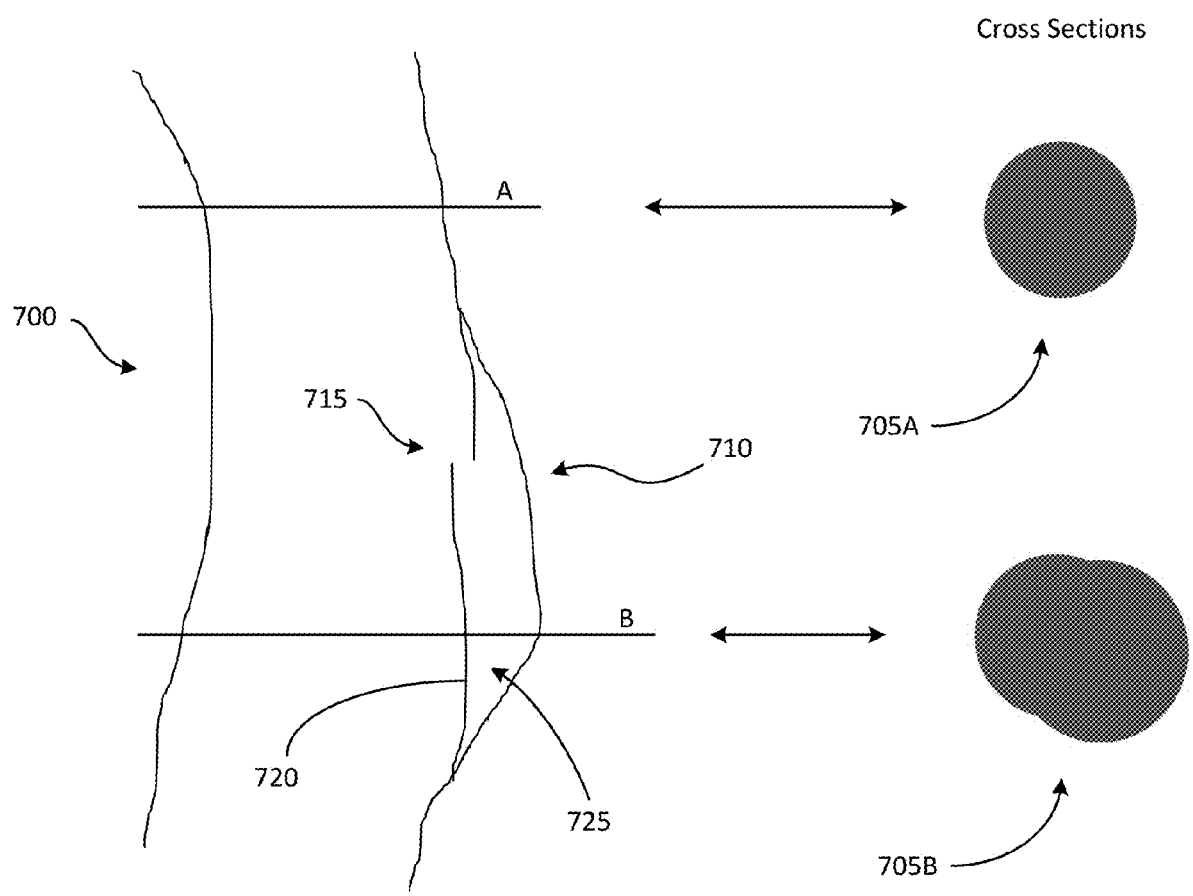
FIG. 9 illustrates the vessel of FIG. 8 with a dissection at the aneurysm and two cross sections of the vessel with the dissection at the aneurysm.

FIG. 9 illustrates the vessel 700 with a dissection 715 at the aneurysm 710 (without contrast). As seen in FIG. 9, the dissection 715 is the result of a tear in an intima 720 of the vessel 700. The tear in the intima 720 (the dissection 715) allows blood to leak into a media 725 of the vessel 700 (creating a false lumen). As noted above, with respect to non-contrast images, the intima 720 and the media 725 of the vessel 700 are typically too thin and low in contrast to capture in non-contrast images. For example, the second cross section 705B of FIG. 8 is nearly identical to the second cross section 705B of FIG. 9. As a result, for non-contrast images of the vessel 700, the non-contrast image of the vessel 700 without the dissection 715 at the aneurysm 710 (as seen in FIG. 8) is nearly identical to the non-contrast image of the vessel 700 with the dissection 715 at the aneurysm 710 (as seen in FIG. 9).

Figure 10:
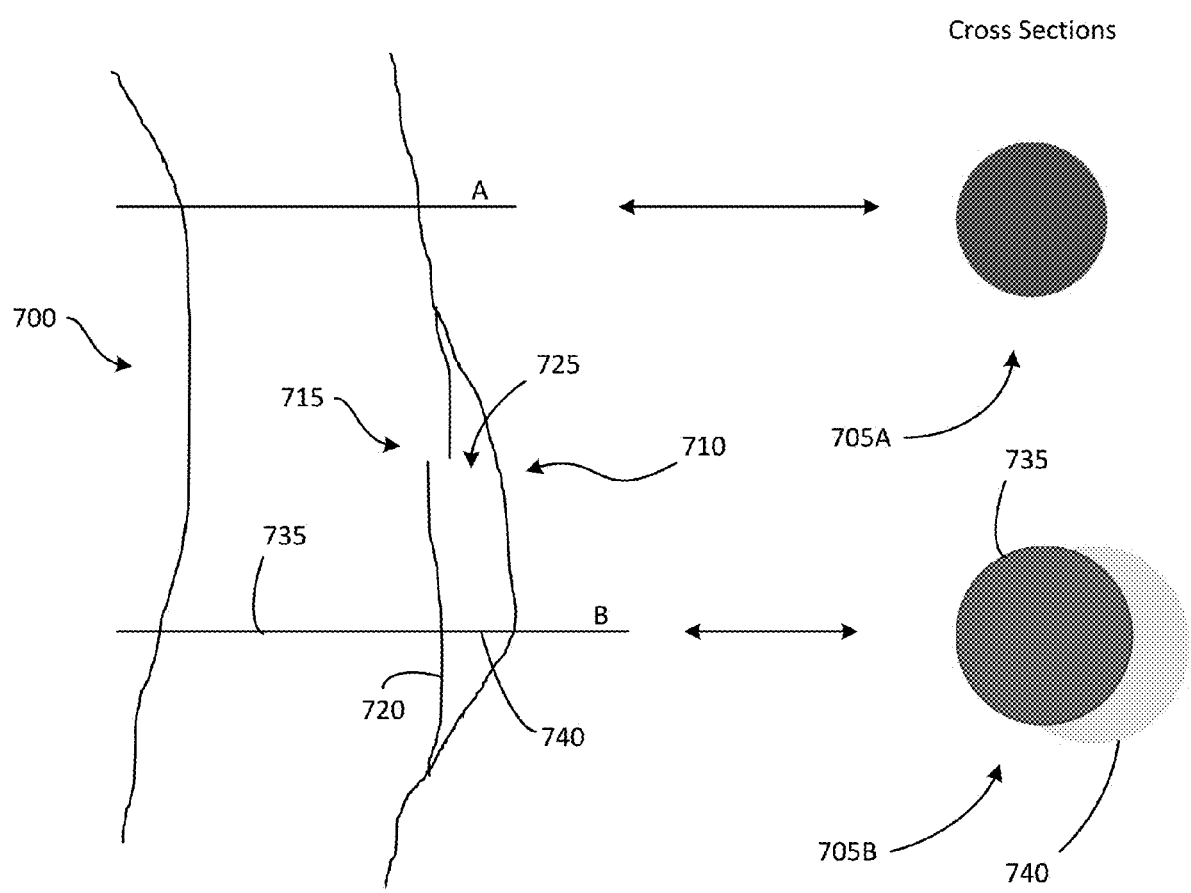
FIG. 10 illustrates the vessel and the two cross sections of the vessel of FIG. 9 with a contrast agent that had been injected.
Figure 11A:
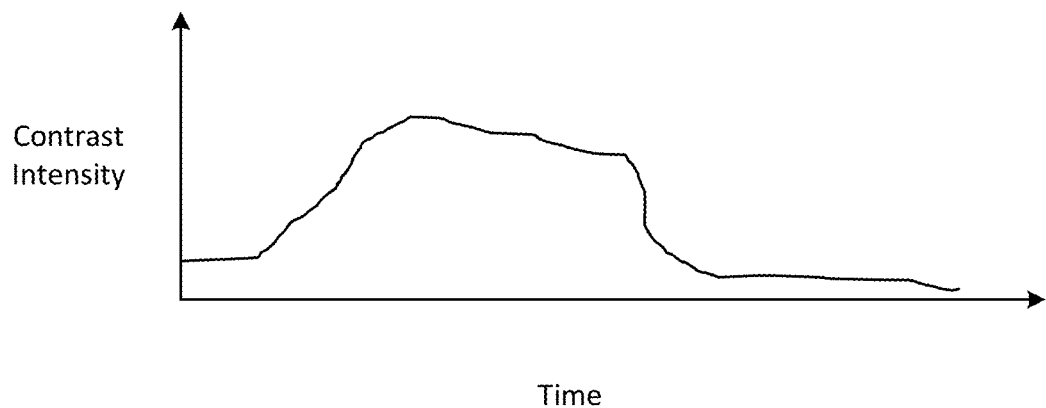
FIGS. 11A and 11B are graphs illustrating contrast agent intensity for a dissected region and a normal region associated with the vessel of FIG. 10.
Figure 11B:
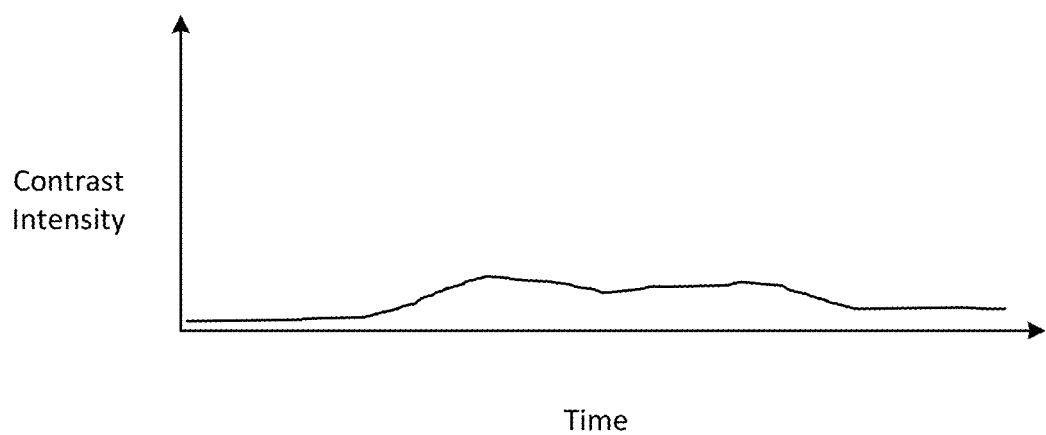
Figure 12:
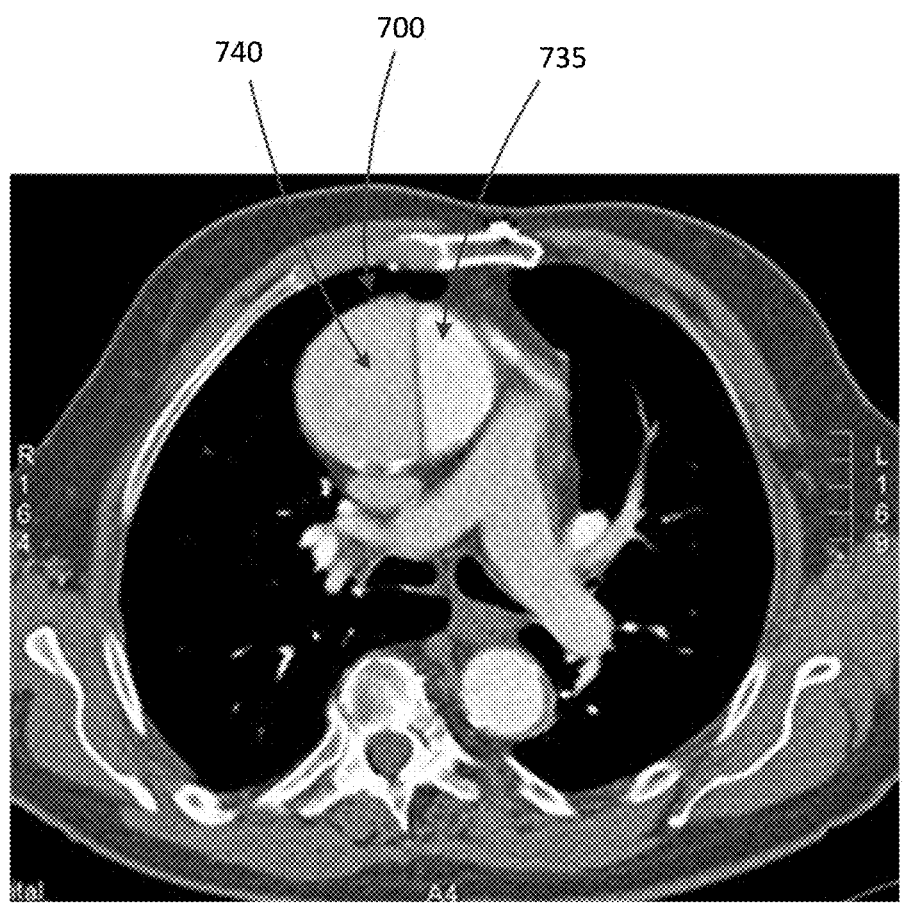
FIG. 12 is a medical image illustrating an aortic dissection having a large amount of contrast agent under the dissection.
Figure 13:
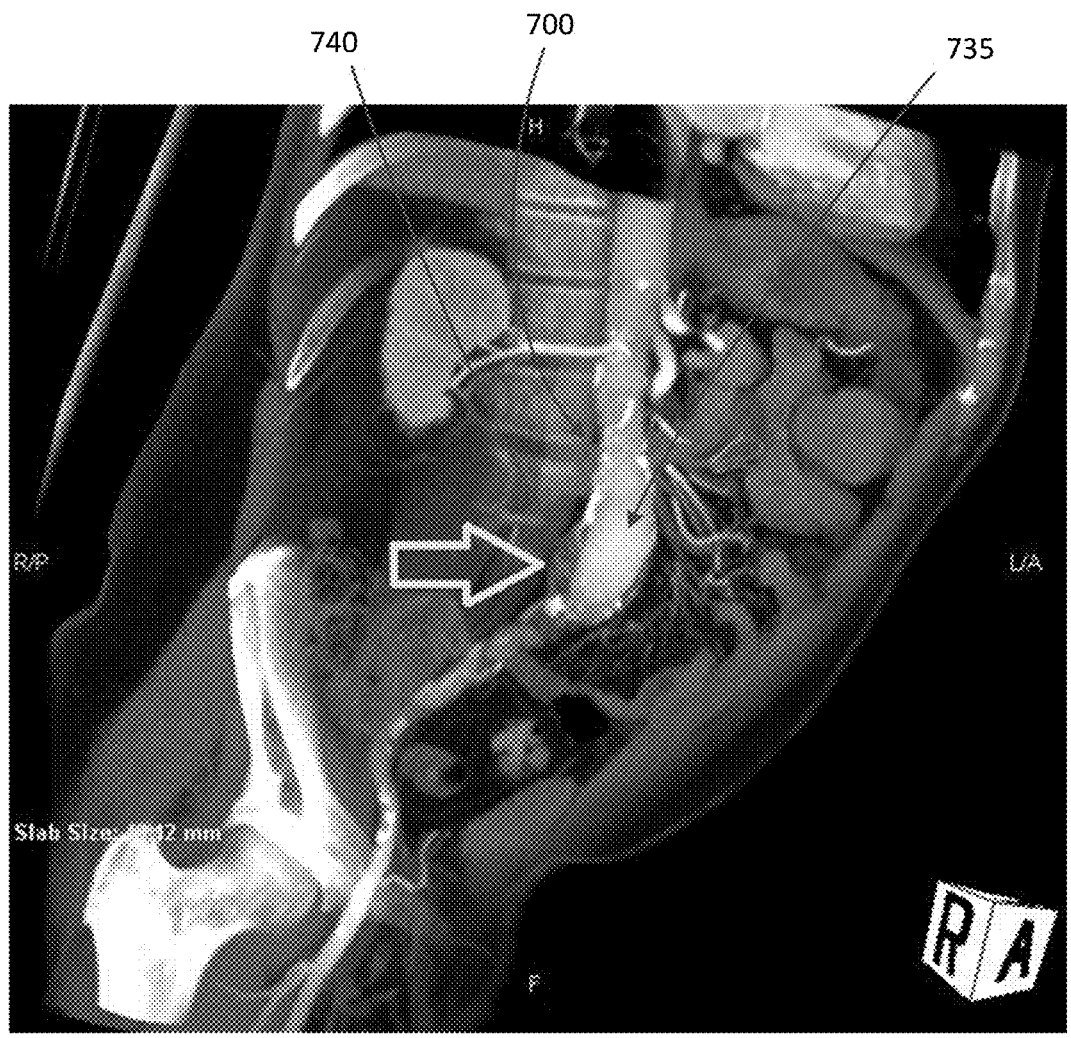
FIG. 13 illustrates an example of a dissection shown as a three-dimensional slab MIP rendering where a false lumen has little to no contrast present.

In comparison, FIG. 10 illustrates the vessel 700 with the dissection 715 at the aneurysm 710 with contrast. As illustrated in FIG. 10, the second cross section 705B includes a normal region 735 (a true lumen) and a dissected region 740 (a false lumen). The normal region 735 and the dissected region 740 are also illustrated along the cross sectional location B for illustrative purposes. The contrast intensity of the normal region 735 is greater than the contrast intensity of the dissected region 740. For example, as a contrast agent travels along the vessel 700, the normal region 735 is exposed to more of the contrast agent than the dissected region 740. For example, FIG. 11A is a graph illustrating a contrast intensity over a period of time with respect to the normal region 735 and FIG. 11B is a graph illustrating a contrast intensity over a period of time with respect to the dissected region 740. As illustrated in the graphs of FIGS. 11A-11B, the normal region 735 (FIG. 11A) is exposed to more of the contrast agent (has a higher contrast intensity) than the dissected region 740 (FIG. 11B). As another example, FIG. 12 is a medical image illustrating an aortic dissection having a large amount of contrast under the dissection. As illustrated in FIG. 12, the vessel 700 includes the normal region 735 (a true lumen) and the dissected region 740 (a false lumen). FIG. 13 is a medical image illustrating a more subtle dissection. In particular, the medical image of FIG. 13 is a three dimensional slab maximum intensity projection (MIP). In the medical image of FIG. 13, the dissection (the dissected region 740) has little to no contrast present in comparison to the normal region 735. In other words, as seen in FIG. 13, the dissected region 140 is lighter than the normal region 735.

Accordingly, as noted above, visualization of non-contrast CT dissections is very difficult via standard means and may be missed as incidental findings in a contrast CT. Thus, embodiments described herein provide enhanced visualization of a dissection using the centerline detection methods and systems described above and, in particular, uses the methods and systems described above to extract a vessel outline in a non-contrast image set and a contrast image set. As described in more detail below, these techniques can be used to identify the true lumen contour, containing both the true lumen and the dissected false lumen, even when there is little or no contrast in the false lumen. The detected dissected region can then be used to display the vessel in a straightened format and allow for further manipulations to better visualize the region.

Figure 14:
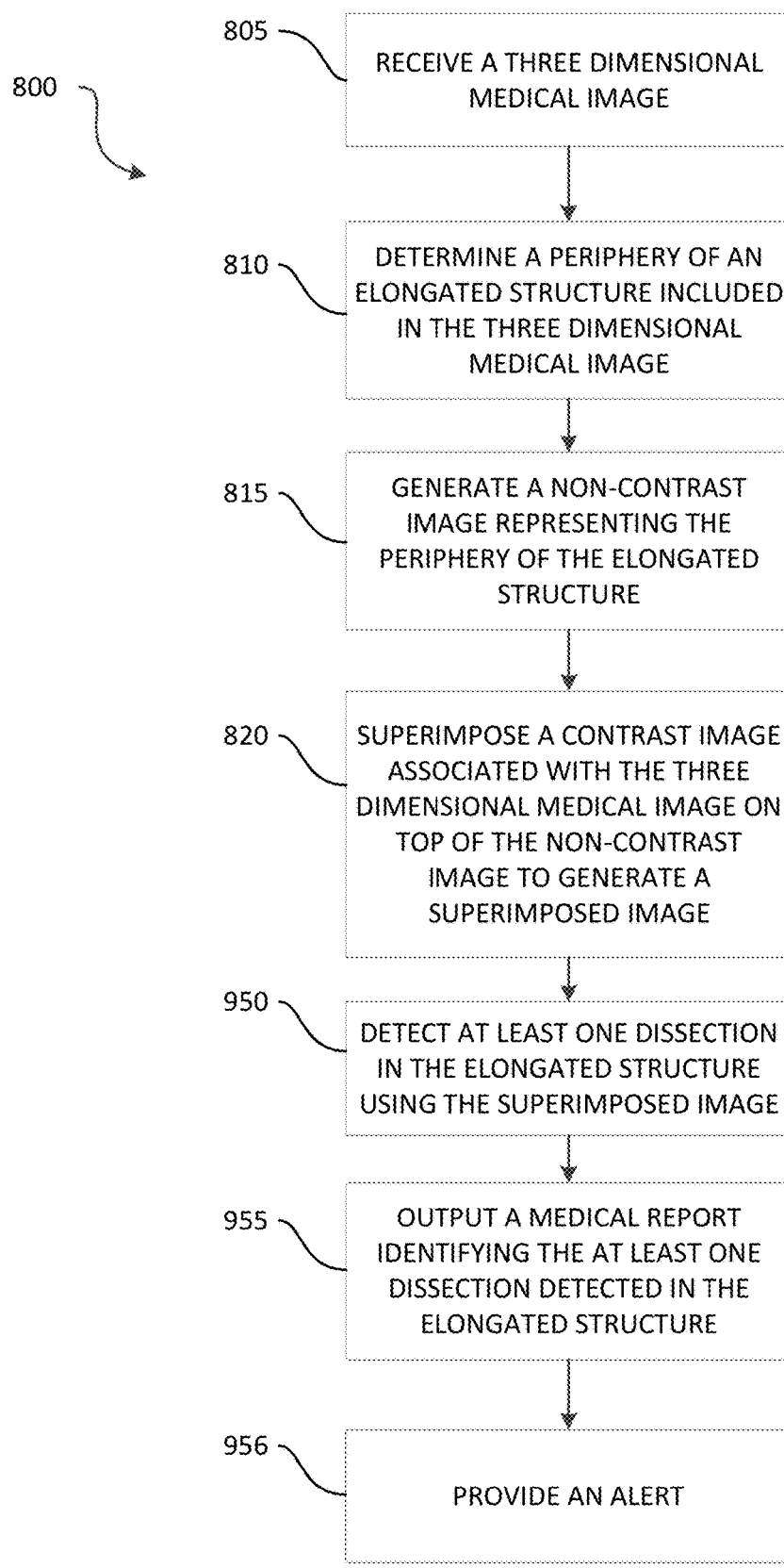
FIG. 14 is a flowchart illustrating a method for detecting a vascular dissection in an elongated structure in a three dimensional medical image according to some embodiments.

For example, FIG. 14 is a flowchart illustrating a method 800 for detecting a vascular dissection in an elongated structure (for example, the vessel 700) in a three dimensional medical image. The method 800 is described here as being performed by the server 205 (the electronic processor 250 executing instructions). However, as noted above, the functionality performed by the server 205 (or a portion thereof) may be performed by other devices, included, for example, the user device 210 (via the electronic processor 225 executing instructions).

As illustrated in FIG. 14, the method 800 includes receiving, with the electronic processor 250, a three dimensional medical image (at block 805). As noted above, the image repository 215 may store a plurality of three dimensional medical images including elongated structures, such as the vessel 700. Accordingly, in some embodiments, the electronic processor 250 receives the three dimensional medical image from the image repository 215. Alternatively or in addition, in some embodiments, one or more three dimensional medical images may be stored at additional or different databases, servers, devices, or a combination thereof. Accordingly, in some embodiments, the electronic processor 250 receives the three dimensional medical image from additional or different databases, servers, devices or a combination thereof. The three dimensional medical image received by the server 105 may be based on a request received from the user device 210. However, in other embodiments, the detection process performed by the server 205 may be performed in response to other triggering events, including, for example, the generation and storage of a new medical exam or study (one or more three dimensional medical images) in the image repository 215.

After receiving the three dimensional medical image from the image repository 215 (at block 805), the electronic processor 250 determines a periphery of the elongated structure included in the three dimensional medical image (at block 810). In some embodiments, the electronic processor 250 determines the periphery of the elongated structure included in the three dimensional medical image using machine learning. For example, in some embodiments, the electronic processor 250 performs one or more of the methods described above with respect to determining a centerline in a three dimensional medical image to determine the periphery of the elongated structure included in the three dimensional medical image (in a non-contrast image set). Alternatively or in addition, the electronic processor 250 performs one or more of the methods described above with respect to determining a centerline in a three dimensional medical image to determine the periphery of the elongated structure included in the three dimensional medical image (in a contrast image set).

In some embodiments, the electronic processor 250 extracts an enhancing part and a non-enhancing part of the vessel 700 from a single contrast CT image (the three dimensional medical image received at block 805). For example, in some embodiments, the electronic processor 250 determines the periphery of the elongated structure (the vessel 700) by determining a centerline corresponding to the vessel 700 (using one or more of the methods described above) and determining "transverse to the centerline" cuts (cross sections) to obtain segmentation of the enhancing part of the vessel 700 and the non-enhancing part of the vessel 700. In some embodiments, the electronic processor 250 determines a difference between the segmentation of the enhancing part of the vessel 700 and the non-enhancing part of the vessel 700 to provide quantity that may be used for detecting the dissection 715 in the vessel 700.

Alternatively or in addition, in some embodiments, the electronic processor 250 determines the centerline of the elongated structure (for example, the vessel 700, such as an aorta) included in the three dimensional medical image. After determining the centerline of the elongated structure, the electronic processor 250 then performs a single segmentation of the non-enhancing part of the vessel 700. As described in greater detail below, after determining the non-enhancing part of the vessel 700, the electronic processor 250 may display the non-enhancing part of the vessel 700 (via, for example, the display device 245 of the user device 210), use machine learning to detect the dissection 715, or a combination thereof.

As illustrated in FIG. 14, the method 800 also includes generating, with the electronic processor 250, a non-contrast image representing the periphery of the elongated structure (at block 815). In some embodiments, the non-contrast image is a volume representing the periphery of the elongated structure. The non-contrast image represents an entire periphery (contour) of the elongated structure in the three dimensional medical image. In other words, in some cases, the non-contrast image may represent a periphery of a vessel having both a normal vessel lumen (a true lumen) and a false lumen. In some embodiments, the non-contrast image is represented natively (near black). However, in other embodiments, the non-contrast image is represented with a false color scheme, such as green, pink, red, or the like.

Figure 15A:
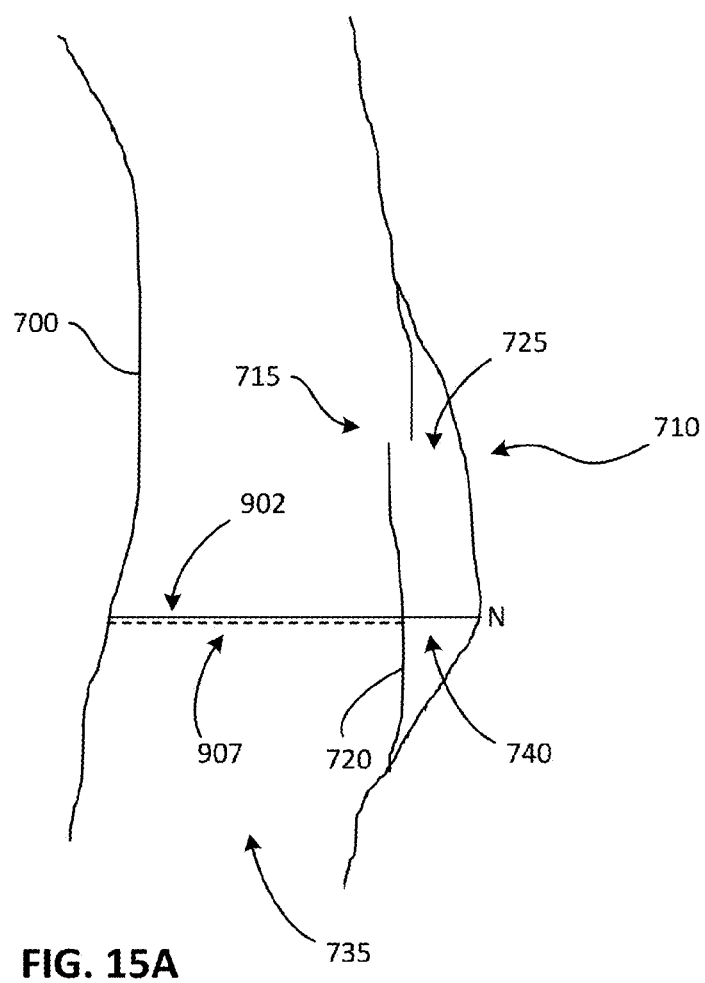
FIG. 15A illustrates a vessel with a dissection at an aneurysm.
Figure 15B:
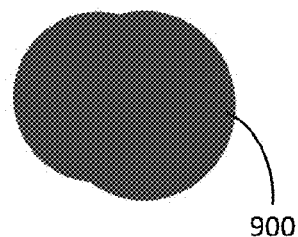
FIG. 15B illustrates a non-contrast image representing a periphery of the vessel of FIG. 15A.

For example, FIG. 15A illustrates the vessel 700 with the dissection 715 at the aneurysm 710. FIG. 15B illustrates a non-contrast image 900. The non-contrast image 900 of FIG. 15B represents the entire periphery of the vessel 700 at a cross sectional location N. As seen in FIG. 15A, the entire periphery of the vessel 700 (at the cross sectional location N) includes both the normal region 735 (a true lumen) and the dissected region 740 (a false lumen). For illustrative purposes, the non-contrast image 900 is represented in FIG. 15A as a solid line 902 traversing the vessel 700 at the cross sectional location N. Additionally, in the illustrated example, the non-contrast image 900 is represented with a false color scheme (red).

After determining the non-contrast image (at block 815), the electronic processor 250 superimposes a contrast image associated with the three dimensional image on top of the non-contrast image (at block 820). The contrast image is a contrast enhanced image of the elongated structure. As noted above with respect to FIG. 10, when an elongated structure has a dissection, a true lumen is exposed to a greater amount of a contrast agent than a false lumen. Therefore, some of the elongated structure is not visible in a contrast image due to the reduced contrast content in the false lumen (see, for example, the second cross section 705B of FIG. 10). Accordingly, the contrast image superimposed on top of the non-contrast image represents a normal vessel lumen of the elongated structure (for example, the normal region 735 of the vessel 700).

Figure 15C:
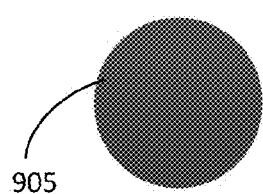
FIG. 15C illustrates a contrast image representing a true lumen of the vessel of FIG. 15A.

FIG. 15C illustrates a contrast image 905. The contrast image 905 represents the normal region 735 (a true lumen) of the vessel 700. For illustrative purposes, the contrast image 905 is represented in FIG. 15A as a dashed line 907 traversing the vessel 700 at the cross sectional location N. As seen in FIG. 15A, the dashed line 907 representing the contrast image 905 only partially traverses the vessel 700. In particular, the dashed line 907 does not include the dissected region 740 of the vessel 700. As noted above, the dissected region 740 is generally not visible in a contrast image. Accordingly, the dashed line 907 representing the contrast image 905 does not include the dissected region 740 of the vessel 700. It should be understood that the dashed line 907 representing the contrast image 905 is off-set from the solid line 902 representing the non-contrast image 900 in FIG. 15A merely for illustrative purposes. However, in actuality, the dashed line 907 representing the contrast image 905 and the solid line 902 representing the non-contrast image 900 in FIG. 15A should be positioned at the same position (on top of each other). In other words, the non-contrast image 900 and the contrast image 905 are both associated with the same cross sectional location (the cross sectional location N) traversing the vessel 700.

Figure 15D:
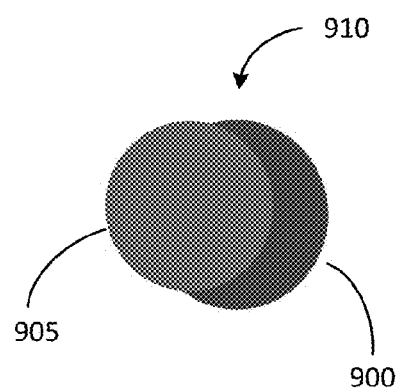
FIG. 15D illustrates a superimposed image generated by superimposing the contrast image of FIG. 15C on top of the non-contrast image of FIG. 15B.

FIG. 15D illustrates a superimposed image 910. As seen in FIG. 15D, the superimposed image 910 includes the contrast image 905 superimposed (overlaid) on top of the non-contrast image. As noted above, the electronic processor 250 generates the superimposed image 910 by superimposing the contrast image 905 on top of the non-contrast image 900 (at block 820).

With reference to FIG. 14, the electronic processor 250 detects at least one dissection in the elongated structure using the superimposed image (at block 950). In some embodiments, the electronic processor 250 detects the at least one dissection in the elongated structure by analyzing the superimposed image 910. For example, the electronic processor 250 may analyze the superimposed image 910 to detect at least one dissection (the dissection 715) in the elongated structure (the vessel 700) using machine learning.

In some embodiments, the electronic processor 250 determines whether there is or is not a dissection using radial measurements of the determined periphery of the elongated structure, a comparison of an area measurement for a contrast image (a true lumen) versus an area measurement for a non-contrast image (a false lumen) in selected slices, or a volumetric false lumen (a non-contrast image) size criteria. The detected region containing the dissection 715 (the false lumen), vascular hematoma, or atheromatous plaque may then be identified by the electronic processor 250.

Alternatively or in addition, in some embodiments, the electronic processor 250 may use a similar technique to detect atheromatous plaques associated with the elongated structure (the vessel 700). When atheromatous plaques are coupled with the aneurysm 710, the atheromatous plaques are a significant danger (of arguably the same scale as the dissection 715) as the atheromatous plaques may rupture and shower a large amount of debris, causing infarctions. In some embodiments, the electronic processor 250 compares pixel density values within the dissected region 740 in the non-contrast series and a contrast series to differentiate the dissection 715 from an atheromatous plaque. There should be no contrast update in an atheromatous plaque but there will typically be some amount contrast visible within the dissection 715. However, this may not necessarily be the case if it is filled with thrombus. The electronic processor 250 may implement an additional artificial intelligence classifier (for example, as a final step) to exclude "turbulent flow anomalies/artifacts" that occur due to incomplete filling from the injection but are otherwise normal. In some embodiments, the electronic processor 250 uses an additional artificial intelligence classifier to include or include or exclude atheromatous plaques.

As discussed above with reference to FIGS. 10-11, a contrast intensity of the dissected region 740 is sharply reduced in comparison to the rest of the vessel 700 (the normal region 735). In particular, the flaps of the dissection 715 impede flow of the contrast agent. Therefore, the contrast agent in the dissected region 740 of the vessel 700 may be sharply reduced in contrast density (intensity), may show a turbulent flow with (sharply) reduced contrast opacity/visualization, or a combination thereof. Accordingly, when the contrast image 905 is superimposed (fused) on top of the non-contrast image 900, the dissection 715 (the boundary between the contrast image 905 and the non-contrast image 900) is easily visible (as illustrated in FIG. 15D).

In some cases, there may be smaller false positive regions due to turbulence in the flow or possibly due to pulsatile motion of the elongated structure (the vessel 700). Additionally, a type of dissection and whether there is a flap opening "upstream" into the flow may change the level of contrast seen in the dissected region 725 (between the dissected flaps and the aneurysm 710 periphery). A small dissection with a flap opening only upstream, results in a worst case for contrast filling the dissection 715 (least visibility). A small flap opening or a flap opening only downstream allows for the least amount of contrast filling the dissection 715 (best case).

Figure 16:
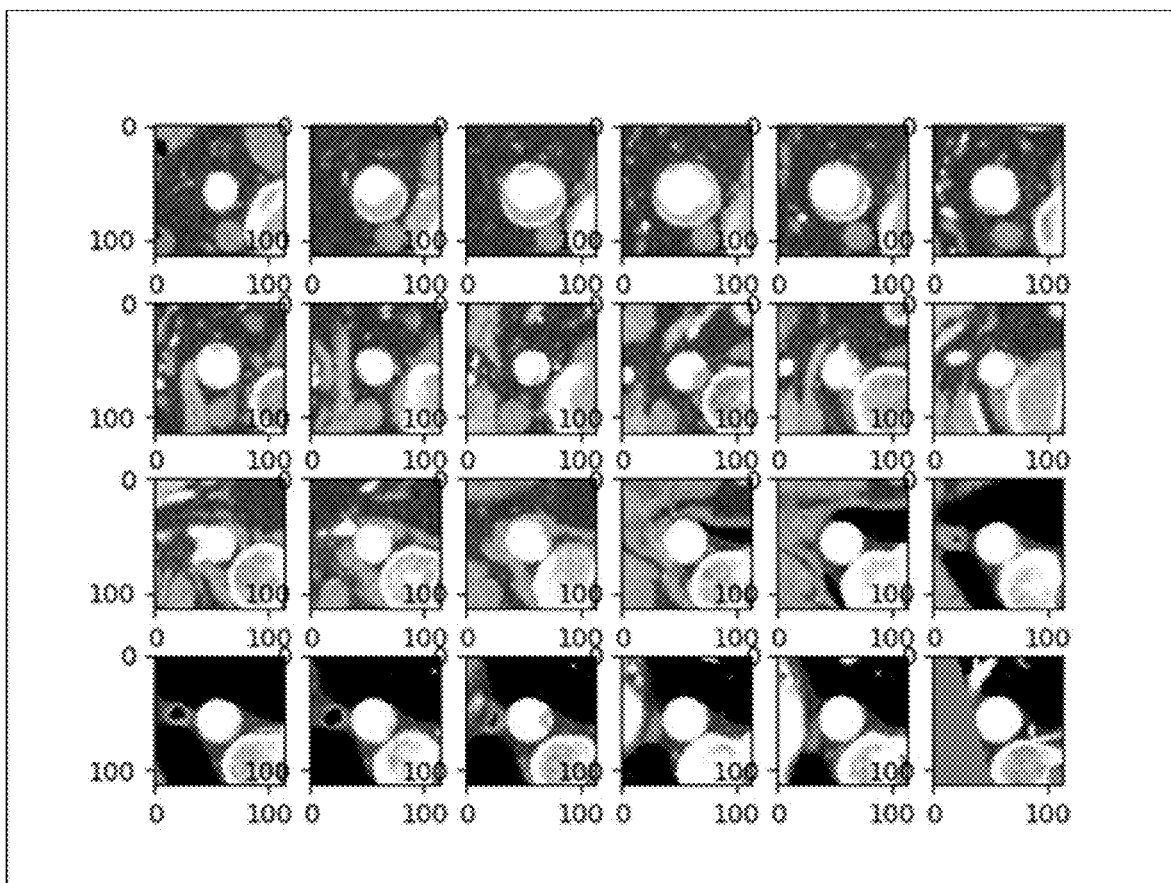
FIG. 16 is an example study including a series of slices.
Figure 17:
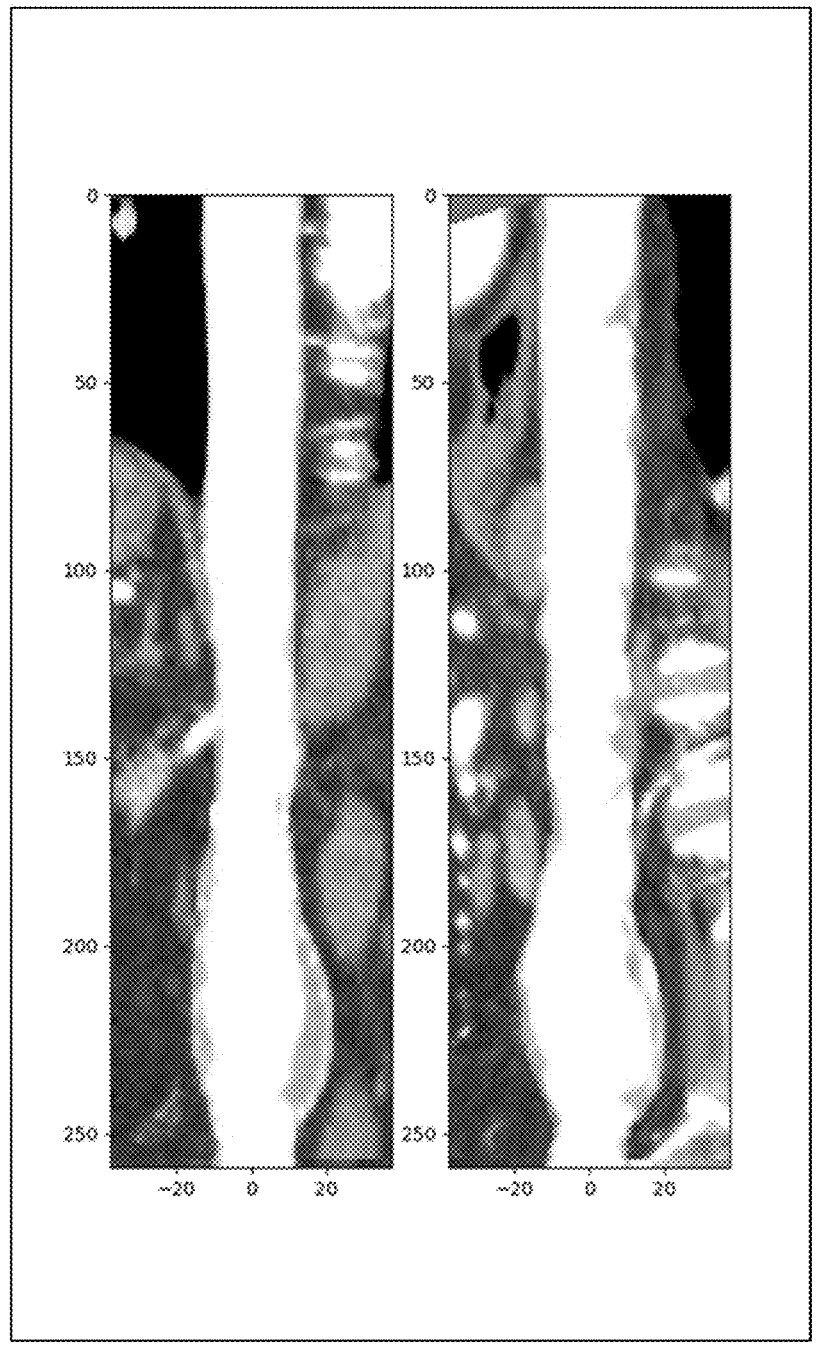
FIG. 17 illustrates a straightened and curved reformat image of the example study of FIG. 6.

As illustrated in FIG. 14, the electronic processor 250 outputs a medical report identifying the at least one dissection detected in the elongated structure (at block 955). In some embodiments, the medical report includes the superimposed image 910 or a plurality of superimposed images 910, where each of the plurality of superimposed images 910 correspond to a different cross sectional location traversing the elongated structure. For example, FIG. 16 illustrates a series of slices. The series of slices includes a plurality of superimposed images 910 corresponding to various cross sectional locations traversing the elongated structure (the vessel 700). As seen in FIG. 16, the non-contrast image 900 (the dissected region 740) included in each of the plurality of superimposed images 910 is represented with a false color scheme (red). In other words, the dissected region 740 included in one or more of the series of slices of in FIG. 16 is depicted in red. As another example, FIG. 17 illustrates a straightened/curved reformatted image. FIG. 17 illustrates the dissected region 740 of the vessel 700 in a false color scheme (red).

In some embodiments, the electronic processor 250 provides (generates) an alert (at block 956). The alert may be sent to a PACS or other worklist in response to detecting one or more dissections in the elongated structure of the three dimensional medical image. Although FIG. 14 illustrates providing an alert (at block 956) as a separate step from outputting the medical report (at block 955), it should be understood that, in some embodiments, the electronic processor 250 may provide the alert in addition to or as an alternative to outputting the medical report identifying the at least one dissection detected in the elongated structure (at block 955). In other words, in some embodiments, outputting the medical report (at block 955) includes providing an alert.

In some embodiments, the electronic processor 250 increases a priority level (or an acuity scoring) of a medical study associated with the three dimensional medical image in response to detecting one or more dissections in the elongated structure of the three dimensional medical image. By increasing the priority level of the medical study, the medical study (the three dimensional medical image) may be acted on more urgently for reading. Alternatively or in addition, in some embodiments, the electronic processor 250 provides the alert by providing the alert to an emergency room, routing the medical study to a particular specialist (for example, a specialist radiologist) or a particular practice (for example, a teleradiology practice) for urgent reading, directly notifying an attending physician, or a combination thereof. Accordingly, embodiments described herein provide alerting that may escalate the management of a medical study or medical case (associated with a detected dissection) even where there is no radiologist immediately available (for example, at a small community hospital at 3:00 a.m. handling an emergency department visit).

Accordingly, embodiments described herein provide vessel edge detection (via artificial intelligence) that determines an entire vessel perimeter (periphery) such that the contrast will be seen. Advantages of the embodiments described herein include determining a true vessel contour (periphery) that includes both the true lumen and the dissected false lumen that may be clearly demonstrated, even in the cases where there is little or no contrast in the false lumen. This combined image (for example, the superimposed image 910) may then clearly demonstrate the dissected region 740. In some embodiments, further image processing may display the vessel 700 in a straightened format (as seen in FIG. 17) and allow further manipulations to better visualize the dissected region 740.

Another possibility of detection and classification of the dissection 715 is to use aorta centerline to extract series of transverse cuts (as described above). The extracted series of transverse cuts may be classified for dissection and severity of dissection using machine learning and methods such as long-short-term-memory (LS™) neural nets or other approaches for processing the series of transverse cuts. The set of transverse slices constitute a three-dimensional image sub-volume with two transverse dimensions and one dimension defined by a direction of an aorta centerline. The volume may be analyzed by deep learning classifier that determines whether an AAS is present, differentiates between various types of AAS (for example, a dissection, a hematoma, or an ulcer) and AAS not present, and, when a dissection is present, differentiates a type (for example, Stanford type A or Stanford type B), a location, and an extent.

Alternatively or in addition, in some embodiments, a vascular dissection (the dissection 715) is detected as described above but with respect to a contrast study when enhancing regions and non-enhancing regions are determined. In such embodiments, the electronic processor 250 detects the periphery of the vessel using a non-contrast series, a contrast series, or both. In other words, the electronic processor 250 provides the best illustration of the outermost vessel contours (the periphery of the elongated structure) and compares the best illustration to a contrast containing vessel contours of the contrast series.

In such embodiments, the electronic processor 250 performs a registration technique against a non-contrast series and a contrast series to determine a best illustration of the periphery of the elongated structure. Use of a patient frame of reference between a pre-contrast series and a post contrast series may result in registration errors due to patient motion. Conventional automated registration techniques will likely fail in the pre-contrast and post-contrast registration. Accordingly, the detected centerlines may be utilized as the primary registration reference between a pre-contrast series and a post-contrast series with other anatomical landmarks (for example, the spine) being secondary references. In some embodiments, a patient's ribs are generally ignored due to the patient's breathing.

For example, the electronic processor 250 may determine a first periphery of the elongated structure included in the three dimensional medical image. The first periphery may be associated with an enhancing part of the elongated structure (for example, a contrast series). The electronic processor 250 may also determine a second periphery of the elongated structure included in the three dimensional medical image. The second periphery may be associated with a non-enhancing part of the elongated structure (for example, a non-contrast series). The electronic processor 250 may determine whether the first periphery or the second periphery best illustrates an outermost periphery of the elongated structure. The electronic processor 250 then generates a base image representing the best illustration of the periphery of the elongated structure. For example, the base image may represent either the first periphery or the second periphery based on whether the first periphery or the second periphery provides the best illustration of the outermost periphery of the elongated structure.

Similar to method 800 (as illustrated in FIG. 14), the electronic processor 250 then superimposes a contrast image, such as the contrast image 905, associated with the three dimensional image on top of the base image representing the best illustration of the periphery of the elongated structure to generate a superimposed image, such as the superimposed image 910. The electronic processor 250 uses the superimposed image to detect the at least one dissection in the elongated structure and outputs the medical report identifying the at least one dissection detected in the elongated structure (as described above).

Alternatively or in addition, in some embodiments, the electronic processor 250 detects a vascular dissection in the elongated structure using a density profile. In particular, the electronic processor 250 detects a "blip" in a density blood pool that is indicative of the dissection 715. The difficulty is that there is little difference in intensity between the blood, the dissected intima and media, and any thrombus that may exist between the dissection 715 and the vessel wall. For instance, normal blood intensity without contrast is on the order of 13-50 Hounsfield Units (HU) or 45-65 HU. A vessel wall is expected to be in the range of 13-60 r, which is nearly the same density range as the blood. Muscle is +35-55 HU, which may be similar to the vessel wall density. Calcifications are ~130-600 HU. Atheromatous plaques are 14-60 HU, which may be attached to the vessel wall. A thrombus is +50 to +75 (may have thrombus in the dissected region 715 of the aneurysm 710).

Figure 18A:
FIGS. 18A-18B illustrate an example of a calcification that appears on top of an atheromatous plaque and visible in adjacent slices.
Figure 18B:

Calcifications and atheromatous plaques are normally attached to the vessel wall. In the case of a dissection, calcifications and atheromatous plaques may either break free (causing problems elsewhere) or remain attached to the vessel intima. In the case where calcifications and atheromatous plaques are attached to the dissected flaps, the occurrence of these abnormalities being "mid-vessel" and not being at the vessel periphery may be an indication of a dissection. Atheromatous plaques are more difficult to visualize but are displayed in competitive cardiac CT applications. Calcifications are relatively easy to visualize. However, differentiating between a calcification on top of an atheromatous plaque versus a calcification that is a dissection may be difficult. For example, FIGS. 18A-18B illustrate a calcification that is on top of an atheromatous plaque and visible in adjacent slices.

Figures 19A, 19B, 19C:
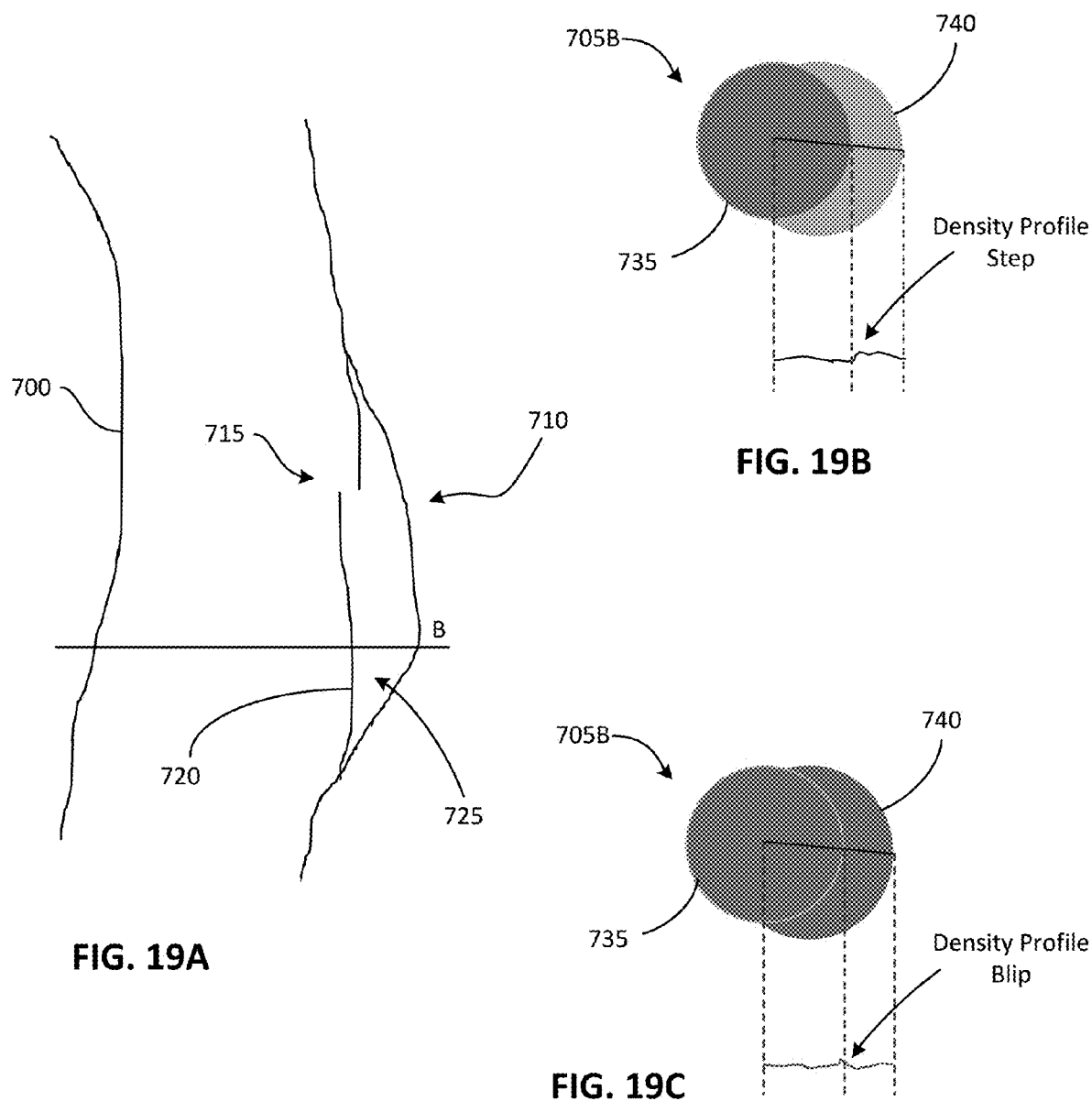
FIG. 19A illustrates a vessel with a dissection at an aneurysm.
FIG. 19B illustrates a cross section of the vessel of FIG. 19A when a thrombus is present and no contrast agent is present (so called "no contrast study").
FIG. 19C illustrates a cross section of the vessel of FIG. 19A when a thrombus is not present and no contrast agent is present (so called "no contrast study").

Once a vessel centerline is detected a radial density profile at each slice may be generated and then the density gradient calculated (simplistically $1^{st}$ and $2^{nd}$ order derivative filters) to find the dissected region 740 (the dissection 715). For example, FIG. 19A illustrates the vessel 700 with the dissection 715 at the aneurysm 710. FIG. 19B illustrates a density profile step associated with the second cross section 705B when a thrombus is present. As seen in FIG. 19B, the step illustrated in the density profile step indicates the dissection 715. FIG. 19C illustrates a density profile blip associated with the second cross section 705B when a thrombus is not present. As seen in FIG. 19C, the blip illustrated in the density profile blip indicates the dissection 715.

The difficulty, is the "blip" or "step" in the density profile may be on the order of a noise level of the blood pool in the vessel 700. Accordingly, in some embodiments, the electronic processor 250 performs a three dimensional analysis process to extract the dissection contour from the noise. In some embodiments, the electronic processor 250 uses image processing, such as slice averaging of maximum intensity projection (MIP) of slabs/thick slice reconstructions. Additionally, in some embodiments, the electronic processor 250 implements LSTM to provide the ability to operate within a slice volume rather than on individual slices.

Figure 20:
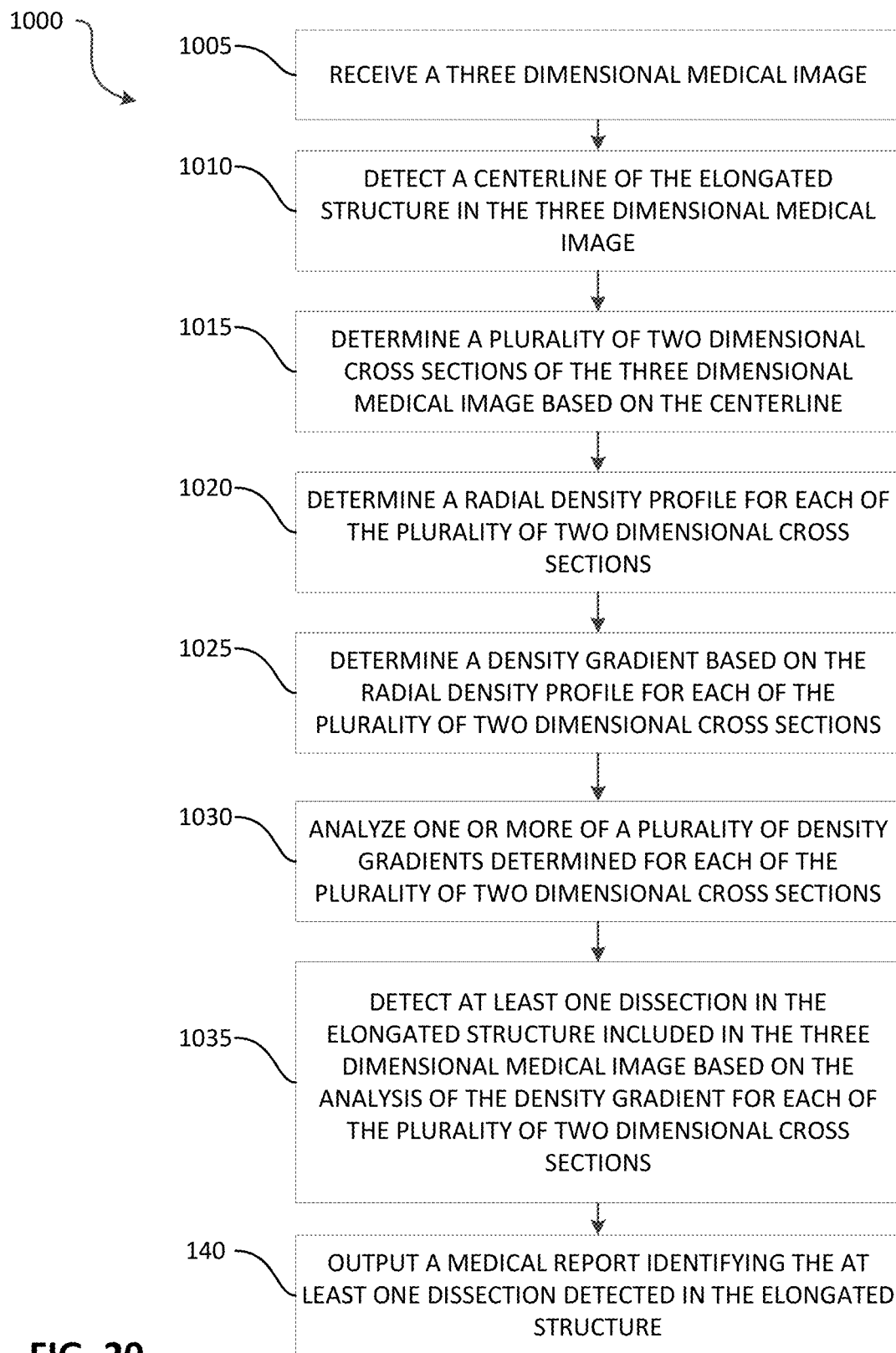
FIG. 20 is a flowchart illustrating a method for detecting a vascular dissection in an elongated structure in a three dimensional medical image according to some embodiments.

For example, FIG. 20 is a flowchart illustrating a method 1000 for detecting a vascular dissection in an elongated structure (for example, the vessel 700) in a three dimensional medical image according to some embodiments. The method 800 is described here as being performed by the server 205 (the electronic processor 250 executing instructions). However, as noted above, the functionality performed by the server 205 (or a portion thereof) may be performed by other devices, included, for example, the user device 210 (via the electronic processor 225 executing instructions).

As illustrated in FIG. 20, the method 1000 includes receiving, with the electronic processor 250, a three dimensional medical image (at block 1005). With respect to block 1005 of method 1000, the electronic processor 250 receives the three dimensional medical image as similarly described above with respect to block 805 of FIG. 14.

After receiving the three dimensional medical image (at block 1005), the electronic processor 250 detects a centerline of the elongated structure in the three dimensional medical image (at block 1010) and determines a plurality of two dimensional cross sections of the three dimensional medical image based on the centerline (at block 1015). The electronic processor 250 detects the centerline of the elongated structure and determines the plurality of two dimensional cross sections using one or more of the methods described above with respect to system 200.

As illustrated in FIG. 20, the electronic processor 250 also determines a radial density profile for each of the plurality of two dimensional cross sections (at block 1020) and determines a density gradient based on the radial density profile for each of the plurality of two dimensional cross sections (at block 1025). After determining the radial density profiles and the density gradients for each of the plurality of two dimensional cross sections (at blocks 1020 and 1025), the electronic processor 250 analyzes one or more density gradients included in the plurality of density gradients determined for each of the plurality of two dimensional cross sections (at block 1030). In some embodiments, the electronic processor 250 analyzes the one or more density gradients included in the plurality of density gradients using machine learning. Based on the analysis of the one or more of the plurality of density gradients determined for each of the plurality of two dimensional cross sections, the electronic processor 250 detects at least one dissection in the elongated structure included in the three dimensional medical image (at block 1035).

For example, in some embodiments, the electronic processor 250 analyzes the density gradients for each of the plurality of two dimensional cross sections by comparing a first density gradient of a first two dimensional cross section included in the plurality of two dimensional cross sections with a second density gradient of a second two dimensional cross section included in the plurality of two dimensional cross sections. The electronic processor 250 may detect the at least one dissection in the elongated structure included in the three dimensional medical image based on the comparison of the first density gradient of a first two dimensional cross section included in the plurality of two dimensional cross sections with a second density gradient of a second two dimensional cross section included in the plurality of two dimensional cross sections. Accordingly, in some embodiments, the electronic processor 250 detects the at least one dissection of the elongated structure included in the three dimensional medical image by determining an intensity difference between the first density gradient of the first two dimensional cross section included in the plurality of two dimensional cross sections and the second density gradient of the second two dimensional cross section included in the plurality of two dimensional cross sections.

The electronic processor 250 outputs a medical report identifying the at least one dissection detected in the elongated structure (at block 1040). With respect to block 1040 of method 1000, the electronic processor 250 outputs the medical report identifying the at least one dissection detected in the elongated structure as similarly described above with respect to block 955 of FIG. 14.

Alternatively or in addition, the methods and systems described herein may be used to track (or monitor) a status of an aneurysm (with or without a dissection) over a period of time (multiple time points). In such embodiments, registration between the multiple time points may be performed. By performing such registration, aneurysm progression may be tracked. For example, an aneurysm progression that needs treatment (even through a signal study indicates that the aneurysm is within "normal" bounds) may be highlighted.

It should be understood that embodiments described above should not be considered limiting. For example, the embodiments described above are not limited medical uses. The embodiments described above may be applied to different types of images for different types of elongated structures. Additionally, the embodiments described herein are not limited to aortic dissections. The embodiments described above may be applied to different types of arterial or venous vessels.

Thus, the embodiments herein provide, among other things, a system for determining the centerline in a three dimensional image using deep learning, wherein the deep learning is performed using a training set of training examples generated using reference points provided for a subset of slices of a three dimensional image. Alternatively or in addition, embodiments herein provide, among other things, a system for detecting a vascular dissection in an elongated structure. Various features and advantages of the invention are set forth in the following claims.

What is claimed is:

1. A system for detecting a vascular dissection in an elongated structure in a three dimensional medical image, the system comprising:
   an electronic processor configured to receive the three dimensional medical image,
   determine a first periphery of the elongated structure included in the three dimensional medical image, wherein the first periphery is associated with an enhancing part of the elongated structure,
   determine a second periphery of the elongated structure included in the three dimensional medical image, wherein the second periphery is associated with a non-enhancing part of the elongated structure,
   determine whether the first periphery or the second periphery best illustrates an outermost periphery of the elongated structure,
   generate a base image representing either the first periphery of the elongated structure or the second periphery of the elongated structure based on whether the first periphery or the second periphery best illustrates an outermost periphery of the elongated structure,
   superimpose a contrast image associated with the three dimensional image on top of the base image to generate a superimposed image,
   detect at least one dissection in the elongated structure using the superimposed image, and
   output a medical report identifying the at least one dissection detected in the elongated structure.

2. The system of claim 1, wherein the electronic processor is configured to determine the second periphery of the elongated structure by
   determining a centerline of the elongated structure, and
   detecting a plurality of two dimensional cross sections of the three dimensional medical image based on the centerline.

3. The system of claim 1, wherein the electronic processor is configured to determine the second periphery of the elongated structure by
   determining a centerline of the elongated structure, and
   performing a single segmentation of the non-enhancing part of the elongated structure.

4. The system of claim 1, wherein the electronic processor is configured to determine the first periphery of the elongated structure and the second periphery of the elongated structure by
  determining a centerline of the elongated structure, and
  determining segmentation of the enhancing part of the elongated structure and the non-enhancing part of the elongated structure.

5. The system of claim 1, wherein the electronic processor is configured to provide an alert to a user by at least one selected from a group consisting of providing an alert to an emergency room, routing a medical study associated with the three dimensional medical image to a medical specialist, and directly notifying the medical specialist.

6. The system of claim 1, wherein the electronic processor is further configured to increase a priority level of a medical study associated with the three dimensional medical image.

7. The system of claim 1, wherein the outermost periphery of the elongated structure included in the three dimensional medical image is a vessel contour that includes a true lumen and a false lumen.

8. The system of claim 1, wherein the base image includes a true lumen.

9. The system of claim 1, wherein the electronic processor detects the at least one dissection in the elongated structure by analyzing the superimposed image using machine learning.

10. A method for detecting a vascular dissection in an elongated structure in a three dimensional medical image, the method comprising:
  receiving, with an electronic processor, the three dimensional medical image;
  determining, with the electronic processor, a first periphery of the elongated structure included in the three dimensional medical image, wherein the first periphery is associated with an enhancing part of the elongated structure,
  determining, with the electronic processor, a second periphery of the elongated structure included in the three dimensional medical image, wherein the second periphery is associated with a non-enhancing part of the elongated structure,
  determining, with the electronic processor, whether the first periphery or the second periphery best illustrates an outermost periphery of the elongated structure,
  generating, with the electronic processor, a base image representing either the first periphery of the elongated structure or the second periphery of the elongated structure based on whether the first periphery or the second periphery best illustrates an outermost periphery of the elongated structure,
  superimposing, with the electronic processor, a contrast image associated with the three dimensional image on top of the base image to generate a superimposed image;
  detecting, with the electronic processor, at least one dissection in the elongated structure using the superimposed image; and
  outputting, with the electronic processor, a medical report identifying the at least one dissection detected in the elongated structure.

11. The method of claim 10, wherein determining the second periphery of the elongated structure includes
  determining a centerline of the elongated structure, and
  detecting a plurality of two dimensional cross sections of the three dimensional medical image based on the centerline.

12. The method of claim 10, wherein determining the second periphery of the elongated structure included in the three dimensional medical image includes determining a centerline of the elongated structure, and
  performing a single segmentation of the non-enhancing part of the elongated structure.

13. The method of claim 10, further comprising:
  in response to detecting the at least one dissection in the elongated structure, providing an alert to a user.

14. The method of claim 13, wherein providing the alert to the user includes at least one selected from a group consisting of providing the alert to an emergency room, routing a medical study associated with the three dimensional medical image to a medical specialist, and directly notifying the medical specialist.

15. The method of claim 10, further comprising: in response to detecting the at least one dissection in the elongated structure, increasing a priority level associated with a medical study associated with the three dimensional medical image.

16. The method of claim 10, wherein the outermost periphery of the elongated structure included in the three dimensional medical image includes a vessel contour that includes a true lumen and a false lumen.

17. The method of claim 10, wherein detecting the at least one dissection of the elongated structure includes analyzing the superimposed image using machine learning to detect the at least one dissection of the elongated structure.

18. A non-transitory computer readable medium including instructions that, when executed by an electronic processor, causes the electronic processor to execute a set of functions, the set of functions comprising:
  receiving the three dimensional medical image;
  determining a first periphery of the elongated structure included in the three dimensional medical image, wherein the first periphery is associated with an enhancing part of the elongated structure;
  determining a second periphery of the elongated structure included in the three dimensional medical image, wherein the second periphery is associated with a non-enhancing part of the elongated structure;
  determining whether the first periphery or the second periphery best illustrates an outermost periphery of the elongated structure;
  generating a base image representing either the first periphery of the elongated structure or the second periphery of the elongated structure based on whether the first periphery or the second periphery best illustrates an outermost periphery of the elongated structure;
  superimposing a contrast image associated with the three dimensional image on top of the base image to generate a superimposed image;
  detecting at least one dissection in the elongated structure using the superimposed image; and
  outputting a medical report identifying the at least one dissection detected in the elongated structure.

19. The computer readable medium of claim 18, wherein the set of functions further comprises:
  in response to detecting the at least one dissection in the elongated structure, providing an alert to a user,
  wherein providing the alert to the user includes at least one selected from a group consisting of increasing a priority level associated with a medical study associated with the three dimensional medical image, providing the alert to an emergency room, routing the medical study associated with the three dimensional medical image to a medical specialist, and directly notifying the medical specialist.

20. The computer readable medium of claim 18, wherein determining the second periphery of the elongated structure includes
- determining a centerline of the elongated structure, and
- detecting a plurality of two dimensional cross sections of the three dimensional medical image based on the centerline.

* * * * *

UNITED STATES PATENT AND TRADEMARK OFFICE
CERTIFICATE OF CORRECTION

| | | |
|---|---|---|
| PATENT NO. | : 11,024,029 B2 | Page 1 of 1 |
| APPLICATION NO. | : 16/507840 | |
| DATED | : June 1, 2021 | |
| INVENTOR(S) | : Mark D. Bronkalla et al. | |

It is certified that error appears in the above-identified patent and that said Letters Patent is hereby corrected as shown below:

On the Title Page

Item (72) Inventors,
Please replace "Ben Graf" with -- Benedikt Werner Graf --

Signed and Sealed this
Twenty-second Day of November, 2022

Katherine Kelly Vidal
*Director of the United States Patent and Trademark Office*